US007867450B2

(12) United States Patent
Hanaoka et al.

(10) Patent No.: US 7,867,450 B2
(45) Date of Patent: Jan. 11, 2011

(54) LIQUID DROPLET EJECTING HEAD, INSPECTION DEVICE, AND METHOD OF USING INSPECTION DEVICE

(75) Inventors: Yukihiro Hanaoka, Shiejri (JP); Toshihiko Yokoyama, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 531 days.

(21) Appl. No.: 11/927,937

(22) Filed: Oct. 30, 2007

(65) Prior Publication Data

US 2008/0106577 A1 May 8, 2008

(30) Foreign Application Priority Data

Nov. 8, 2006 (JP) .......................... P2006-302480
Jan. 31, 2007 (JP) .......................... P2007-020555
Jan. 31, 2007 (JP) .......................... P2007-020556

(51) Int. Cl.
*G01N 15/06* (2006.01)
*G01N 33/00* (2006.01)
*G01N 33/48* (2006.01)
*B01L 3/02* (2006.01)

(52) U.S. Cl. .......................... 422/100; 422/103; 347/1; 347/20; 436/180; 73/863; 73/864.81

(58) Field of Classification Search ................ 422/100, 422/103; 347/1, 20
See application file for complete search history.

(56) References Cited

U.S. PATENT DOCUMENTS

| | | | | |
|---|---|---|---|---|
| 7,160,511 | B2 | 1/2007 | Takahashi et al. | |
| 7,311,373 | B2 * | 12/2007 | Higuchi et al. | 347/19 |
| 7,513,592 | B2 * | 4/2009 | Miyazawa | 347/29 |
| 2006/0033773 | A1 * | 2/2006 | Owaki | 347/45 |

FOREIGN PATENT DOCUMENTS

| | | |
|---|---|---|
| JP | 2001-228162 | 8/2001 |
| JP | 2002-116205 | 4/2002 |
| JP | 2002-311036 | 10/2002 |
| JP | 2005-104163 | 4/2005 |
| JP | 2006-35791 | 2/2006 |

* cited by examiner

*Primary Examiner*—Brian J Sines
(74) *Attorney, Agent, or Firm*—Nixon & Vanderhye P.C.

(57) ABSTRACT

A liquid droplet ejecting head includes a nozzle unit having a nozzle capable of ejecting liquid droplets and a pressure generating passage communicating with the nozzle. A driving unit includes a nozzle unit mounting portion and an actuator. The nozzle unit is detachably mounted on the nozzle unit mounting portion, and the actuator changes an inner volume of the pressure generating passage of the nozzle unit in order to eject the liquid droplets from the nozzle of the nozzle unit mounted on the nozzle unit mounting portion.

27 Claims, 15 Drawing Sheets

(INTRODUCTION OF INSPECTION OBJECT)

(SUCTION OF CLEANING LIQUID)

(DISCHARGE OF CLEANING LIQUID)

(SUCTION OF CHEMICAL LIQUID)

(DISPENSATION OF CHEMICAL LIQUID)

(DISCHARGE OF REMAINING CHEMICAL LIQUID)

LIQUID DROPLET EJECTING HEAD, INSPECTION DEVICE, AND METHOD OF USING INSPECTION DEVICE

BACKGROUND

1. Technical Field

The present invention relates to a liquid droplet ejecting head suitable for supply and dispensation of chemical liquids, a test reagent, or the like in a medical care field, a bio technology field, etc.

Moreover, the present invention relates to an inspection device (for example, the inspection device for carrying out inspection such as a general biochemical inspection, an immune inspection, etc.) for carrying out a quantitative analysis and a qualitative analysis by adding chemical liquids to an inspection object (sample) of an inspection chip to react them using the liquid droplet ejecting head, and the use method of the inspection device.

2. Related Art

As disclosed in JP-2002-311036A, an inspection device includes a test reagent dispenser dispensing a test reagent from a test reagent container to a reaction container, an inspection object dispenser dispensing an inspection object from a inspection object container to the reaction container, and a measurement unit of an optical type or the like measuring a reacting status of the inspection object and the test reagent in the reacting container. Since an amount of the detected object of the inspection object is measured in a biochemical test and a clinic test by means of color comparison reaction, absorbance, or the like, it is required to control a dispensation amount of the inspection object and the test reagent with high precision.

For this reason, when dispensing the test reagent and the inspection object, a dispenser of an expensive syringe pump type is generally used. Whenever the inspection object or the test reagent is changed in preparation for the next use, it is required that the dispenser be carefully cleaned, and the waste liquid generated by the cleaning be removed.

Since the expensive syringe pump or the like is used to control a minute dispensation amount with a high precision in a known dispenser, it is not effective to reduce a cost of the inspection device. Additionally, there are problems in the syringe pump in that the structure to move pistons in the inside of inner cylinder is complicated. Moreover, whenever the test drug, test body, or the like is changed, it is required to reliably clean the dispenser so that contamination does not occur. Accordingly, the efficiency of the test work is poor, and it is not proper to carry out various tests in a short time.

For this reason, it is considered to use an ink jet head of an ink jet printer for a dispenser for supplying a minute amount of chemical liquids, test liquids, or the like to an inspection object.

As the ink jet head of the ink jet printer, there is known a piezoelectric ink jet head configured to eject ink droplets using a piezoelectric element. In JP-A-2006-35791 and JP-A-2005-104163, there is disclosed a piezoelectric ink jet head that performs a so-called pulling-knocking operation in which a capacity of an ink passage communicating with an ink nozzle by means of displacement of the piezoelectric element increased and decreased to eject ink droplets.

In the ink jet head, a head maintenance process is carried out in order to prevent the ink nozzle from being clogged. The head maintenance process regularly ejects the ink droplets irrespective of printing or sucks ink from the ink nozzle. When the ink jet head is used as a liquid droplet ejecting head for dispensing chemical liquids or test reagents, it is desirable that the number of the head maintenance processes is reduced to prevent an unnecessary consumption of the chemical liquids or the like. However, if the number of the head maintenance processes is reduced, the nozzle may be clogged easily. Once the nozzle is clogged, the liquid droplet ejecting head must be exchanged, thereby further increasing cost.

Moreover, the dispenser for supplying the chemical liquids or the test liquids is a disposable device in many cases. Accordingly, when the ink jet head and the same structured liquid droplet ejecting head are used as the disposable device, it is not effective in terms of cost.

In the ink jet head using the piezoelectric element, a piezo element is generally used as the piezoelectric element. The piezo element, however, contains much lead, and thus when it is used as a disposable head, it is necessary to properly handle the lead in terms of environmental contamination.

SUMMARY

An advantage of some aspects of the described embodiments is to provide a liquid droplet ejecting head suitable for prevention of an unnecessary consumption of liquids such as chemical liquids, a countermeasure against clogging of a nozzle at low cost, and a disposable device.

Moreover, another advantage of some aspects is to provide the liquid droplet ejecting head that dispenses a minute amount of test reagent or the like with high precision, and thus it is not necessary for a cleaning operation when changing an inspection object and the test reagent.

Furthermore, still another advantage is to provide an inspection device having such a liquid droplet ejecting head and a use method thereof.

According to an aspect of the invention, there is provided a liquid ejecting head including a nozzle unit; and a driving unit, wherein the nozzle unit has a nozzle capable of ejecting liquid droplets and a pressure generating passage communicating with the nozzle, wherein the driving unit has a nozzle unit mounting portion and an actuator, and wherein the nozzle unit is detachably mounted on the nozzle unit mounting portion and the actuator changes the inner volume in the pressure generating passage in order to eject the liquid droplets from the nozzle with the nozzle unit mounted on the nozzle unit mounting portion.

The liquid droplet ejecting head includes the driving unit equipped with the actuator and the nozzle unit detachably mounted on the driving unit. When the nozzle is clogged, the nozzle unit can be detached from the driving unit to be exchanged. In addition, since the driving unit equipped with an expensive actuator such as a piezoelectric element can continue to be used, it is economical.

In particular, when a disposable liquid droplet ejecting head is used, the expensive driving unit equipped with the actuator is not required to be thrown away.

Even when the number of the head maintenance operations is reduced, and thus the nozzle is clogged more frequently, the nozzle unit can be exchanged. Accordingly, the number of the head maintenance operations can be determined in consideration of an amount of liquid unnecessarily consumed by the head maintenance operations and the exchange cost of the nozzle unit. As a result, it is possible to reduce the amount of unnecessarily consumed liquid by reducing the number of the head maintenance operations, compared to a case where an entire liquid droplet ejecting head is exchanged like the prior constructions.

The nozzle unit and the driving unit may be configured as follows. The nozzle unit may have a mount portion detachably mounted on the nozzle unit mounting portion of the driving unit, and the mount portion may have the pressure generating passage and a passage-side vibration plate that constitutes a part of the pressure generating passage and can vibrate in an out-of-plane direction. The nozzle unit mounting portion may have a mount hole, and the driving unit may further include a driving-side vibration plate that is disposed in the mount hole and can vibrate in the out-of-plane direction. The actuator may comprise a piezoelectric element, and the driving-side vibration plate may be disposed at a position that comes in contact with the passage-side vibration plate of the mount portion inserted into the mount hole so as to be vibrated by the piezoelectric element.

In this case, the driving unit may have an elastic member disposed in a position opposite the driving-side vibration plate in the mount hole, and the elastic member may be elastically deformed by the mount portion of the nozzle unit inserted into the mount hole so as to be disposed in a position in which the mount portion can be urged toward the driving-side vibration plate by an elastically restoring force.

In the liquid droplet ejecting head with the above-described configuration, when the mount portion of the nozzle unit is inserted into the mount hole of the driving unit, the elastic member is elastically deformed by the mount portion. The passage-side vibration plate comes in contact with the driving-side vibration plate of the driving unit by the elastically restoring force of the elastic member so as to be retained. Accordingly, when the piezoelectric element vibrates the driving-side vibration plate, the passage-side vibration plate that comes in contact with the driving-side vibration plate is also vibrated, and thus the volume of the pressure generating passage varies. In this way, the liquid pressure in the pressure generating passage varies, and thus it is possible to eject the liquid droplets from the nozzle.

In addition, the mount portion of the nozzle unit is retained in the mount hole of the driving unit by the elastically restoring force of the elastic member. It is possible to simply detach the nozzle unit from the driving unit by extracting the mount portion from the mount hole against the urging force caused by the elastically restoring force.

In this case, a so-called "pulling and knocking", operation, where the volume of the pressure generating passage is once increased, and then the liquid droplets are ejected from the nozzle at the time of decreasing the volume, may be performed. The pulling and knocking operation has advantages in that it can eject a larger amount of liquid droplet by using the pressure generating passage with a small volume than a so-called "pressing and knocking" operation, where the volume of the pressure generating passage is simply decreased to eject the liquid droplets. Moreover, the pulling and knocking operation has advantages in that it is possible to accelerate the ejection speed of the liquid droplets and to eject a small amount of liquid droplet, if necessary, or the like.

In the liquid droplet ejecting head with the above-described configuration, the driving-side vibration plate and the passage-side vibration plate are brought in contact with each other by the elastically restoring force of the elastic member so as to be retained when mounted. Accordingly, the passage-side vibration plate can follow the driving-side vibration plate so as to be displaced in any direction of the vibration.

As a result, it is possible to eject the liquid droplets by means of the "pulling and knocking" operation.

In order to reliably vary the volume of the pressure generating passage by the passage-side vibration plate vibrated by the driving-side vibration plate, the passage-side vibration plate may have a center portion of which a rigidity is higher than that of an outer peripheral portion and a flat contact surface formed in the center portion, the contact surface may come in contact with the driving-side vibration plate, the driving-side vibration plate may have an opposite surface opposite the contact surface and a plurality of protrusions formed on the opposite surface, and the protrusions may come in contact with the contact surface. In this way, according to the vibration of the driving-side vibration plate, it is possible to vibrate the center portion of the passage-side vibration plate to increase the volume of the liquid passage. As a result, the liquid droplets can be reliably ejected.

A back surface of the opposite surface of the driving-side vibration plate may be retained so as to come in contact with a displacement surface of the piezoelectric element.

In addition, the storing portion for supplying the liquids to the pressure generating passage of the nozzle unit, may be disposed apart from the nozzle unit to supply the liquids to the pressure generating passage through a liquid supply tube or the like. The storing unit and the nozzle unit may be incorporated. Moreover, in the piezoelectric element, a stacked piezo element for guaranteeing a sufficient amount of displacement may be used.

According to another aspect, there is provided a multiple liquid droplet ejecting head including a plurality of liquid droplet ejecting heads. In this case, the driving units of the liquid droplet ejecting heads may be connected to each other so as to at least form the multiple driving unit.

According to yet another aspect, an inspection device includes a liquid droplet ejecting head that dispenses the test reagents or the inspection object. The liquid droplet ejecting head corresponds to the liquid droplet ejecting head with the above-described configuration. As the dispenser for dispensing the test reagent or the inspection object, the same liquid droplet ejecting head as an ink jet head of an ink jet printer is employed. Only the nozzle and the ejection pressure generating passage are formed in the disposable nozzle unit accommodating the test reagents and the inspection object. In addition, the expensive actuator such as the piezoelectric element is disposed in the driving unit.

Since a small amount of test reagent or the inspection object to be dispensed can be controlled by employing the liquid droplet ejecting head identical with the ink jet head as the dispenser, it is possible to inspect the inspection object with high precision. When the test reagent or the inspection object is exchanged, it is possible to extract the nozzle unit from the driving unit to exchange for a nozzle unit having a different test reagent or inspection object. Moreover, cleaning of the passages of the test reagent or the injection object of the dispenser is not required. When the test reagent or the inspection object is exhausted, the nozzle unit is discarded. The expensive actuator disposed in the driving unit, however, can be used again, and the assembly is thus cost effective. Moreover, since an inner cylinder of a syringe pump does not come in contact with the piston, durability is also excellent.

The inspection device with the above-described configuration may have a carriage conveying the driving unit to a nozzle unit mount position and a dispensation position. In this case, an inspection table for placing an inspection chip that attaches the liquid droplets ejected from the liquid droplet ejecting head in the dispensation position may be disposed.

The inspection device with the above-described configuration may include a multiple driving unit head having a structure in which a plurality of driving units are connected with each other, and the multiple driving unit may be mounted on the carriage. In this way, the plurality of nozzle units that store the different types of test reagents can be simultaneously conveyed. As a result, it is possible to efficiently dispense the different types of test reagents or the like.

In order to efficiently inspect various types of the test liquids and inspection objects, the inspection device with the above-described configuration may include a magazine for housing the nozzle unit and a nozzle unit conveyance mechanism for extracting the nozzle unit from the magazine to mount the nozzle unit in the driving unit.

According to still another aspect of the invention, there is provided an inspection device including a liquid droplet ejecting head having liquid ejecting and liquid sucking nozzles; a carriage conveying for the liquid droplet ejecting head to a standby position, a liquid ejection position, and a liquid suction position; a liquid storing portion for storing liquids sucked by the liquid droplet ejecting head in the liquid suction position; an inspection table for placing an inspection chip that attaches liquid droplets ejected from the liquid ejecting head in the liquid droplet ejection position; and a head sucking pump for supplying a sucking force required to suck liquids from the nozzle to the liquid droplet ejecting head, wherein the above-described liquid droplet ejecting head is used as the liquid droplet ejecting head.

In the inspection device with the above-described configuration, when the nozzle unit is mounted on the nozzle unit mounting portion of the driving unit, a liquid droplet ejecting head identical with the ink jet head of the ink jet printer is configured. Moreover, the actuator such as the expensive piezoelectric element is mounted not on the nozzle unit, but on the driving unit. The chemical liquids can be dispensed in the manner of moving the liquid droplet ejecting head to the liquid storing portion, sucking an amount of chemical necessary to inspect the inspection object from the nozzle to the storing portion of the nozzle unit by using the head suction pump, and then ejecting the chemical liquids from the nozzle to a predetermined portion of the inspection chip in which the inspection object is supplied by moving the storing portion to the liquid ejection position.

According to exemplary embodiments, the dispensation of the chemical liquids is performed in the manner that the liquid droplets are ejected from the nozzle by using the same mechanism as the ink jet head. Accordingly, it is possible to control the amount of chemical to be dispensed with high precision, and thus the inspection object can be inspected with high precision. When the test reagent or the inspection object is exchanged, it is possible to extract the nozzle unit from the driving unit to exchange for a new nozzle unit. Moreover, cleaning the passages of the test reagent or the injection object of the dispenser is not required. Since the expensive actuator is not mounted on the discarded nozzle unit detached from the driving unit, it is possible to configure the nozzle unit at low cost. As a result, even though the nozzle unit is disposable, cost efficiency is not deteriorated. Moreover, since the inner cylinder of the syringe pump does not come in contact with the piston, durability is also excellent.

Throwing away the discarded nozzle unit that contains the chemical or the like yet is not desirable in terms of environmental contamination. In the inspection device with the above-described configuration, a waste liquid recovery portion may be provided for recovering liquids by sucking the liquids in the nozzle unit through the nozzle in the standby position.

When foreign substances or the like are attached to the empty nozzle unit, the inspection object or the test reagent can be contaminated. Accordingly, inspection precision may be deteriorated. Accordingly, the liquid storing portion may have a chemical liquid storing portion storing chemical liquids for inspecting an inspection object and a cleaning liquid storing portion storing cleaning liquids for cleaning the liquid droplet ejecting head. In this case, it is possible to clean the nozzle unit by sucking the cleaning liquids to the nozzle unit, and then discharging the cleaning liquids to the waste liquid recovery portion.

In the inspection device with the above-described configuration, the carriage may move the liquid droplet ejecting head along a straight head movement route from the standby position to the liquid suction position via the liquid ejection position.

When the inspection table in which the inspection chip supply mechanism supplies the inspection chip can move in a different direction from the head movement path, for example, in a direction perpendicular to the head movement path, a relative position between the nozzle of the liquid droplet ejecting head and the inspection chip can be arbitrarily set.

There are many cases where plural types of the chemical liquids are used in inspecting the inspection object. For this reason, the liquid droplet ejecting head may have the plurality of the driving units and the nozzle units, and in the liquid storing portion, the liquid storing portions corresponding to at least the number of the nozzle units may be disposed, and different chemical liquids may be stored in the liquid storing portions.

The inspection device that includes the waste liquid recovery portion and the cleaning liquid storing portion can be used as follows. A liquid droplet ejecting head is configured by mounting an empty nozzle unit in a driving unit positioned in a standby position. Subsequently, cleaning liquids from a nozzle are sucked by moving the liquid droplet ejecting head to a liquid suction position. Subsequently, the cleaning liquids in the nozzle unit through the nozzle are recovered by returning the liquid droplet ejecting head to the standby position. An amount of chemical required to inspect an inspection object from the nozzle is sucked, and the chemical liquids in the storing portion are collected by moving the liquid droplet ejecting head. The chemical liquids for the inspection chip from the nozzle are ejected by moving the liquid droplet ejecting head to the liquid ejection position. Subsequently, the liquid droplet ejecting head is returned to the standby position.

In this case, at the time of exchanging the nozzle unit mounted on the driving unit, the chemical liquids remaining in the nozzle unit may be recovered to a waste liquid recovery portion through the nozzle in the standby position, and then the nozzle unit may be detached from the driving unit to be discarded.

BRIEF DESCRIPTION OF THE DRAWINGS

The embodiments will be described with reference to the accompanying drawings, wherein like numbers reference like elements.

DESCRIPTION OF EXEMPLARY EMBODIMENTS

Hereinafter, an embodiment will be described with reference to the drawings.

First Embodiment

Liquid Droplet Ejecting Head

Figure 1A:
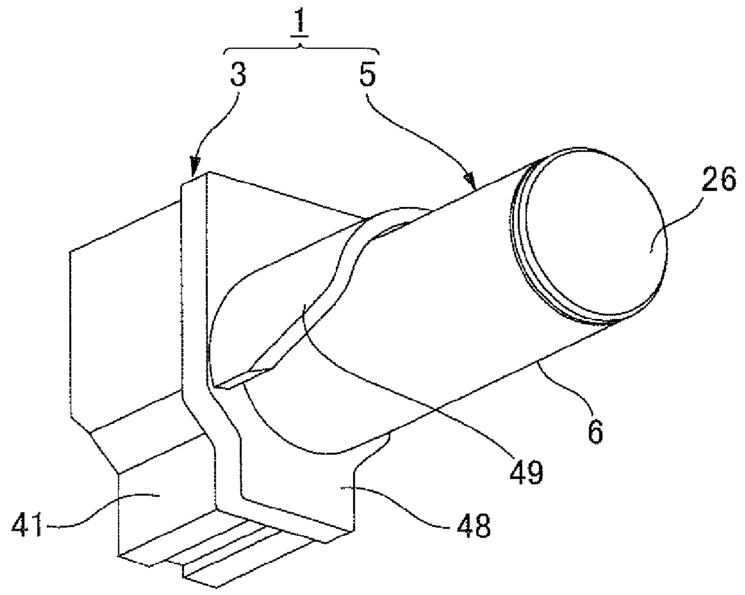
FIGS. 1A and 1B are perspective views illustrating a liquid droplet ejecting head.
Figure 1B:
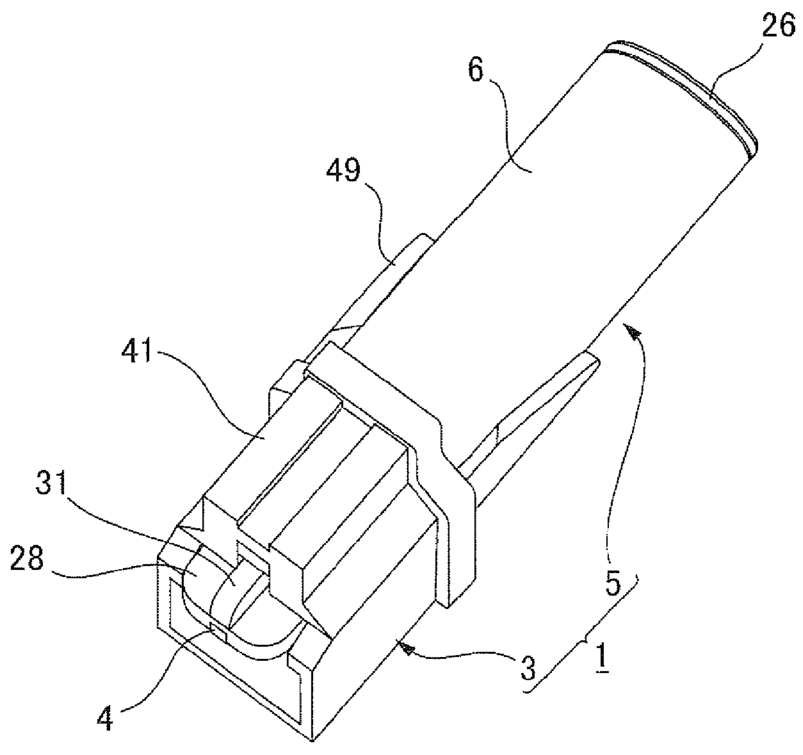
Figure 2A:
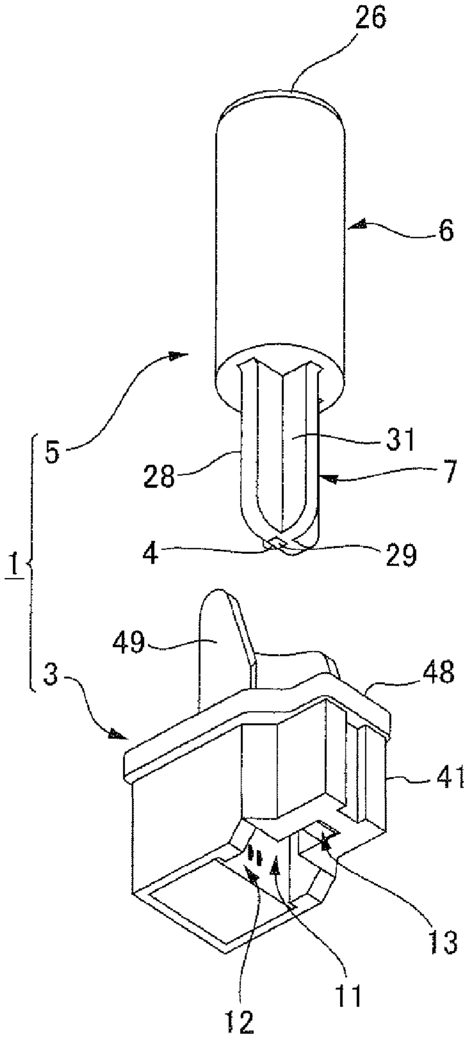
FIGS. 2A and 2B are a perspective view illustrating the detached liquid droplet ejecting head shown in FIGS. 1A and 1B and a longitudinal sectional view illustrating the detached liquid droplet ejecting head shown in FIGS. 1A and 1B, respectively.
Figure 2B:
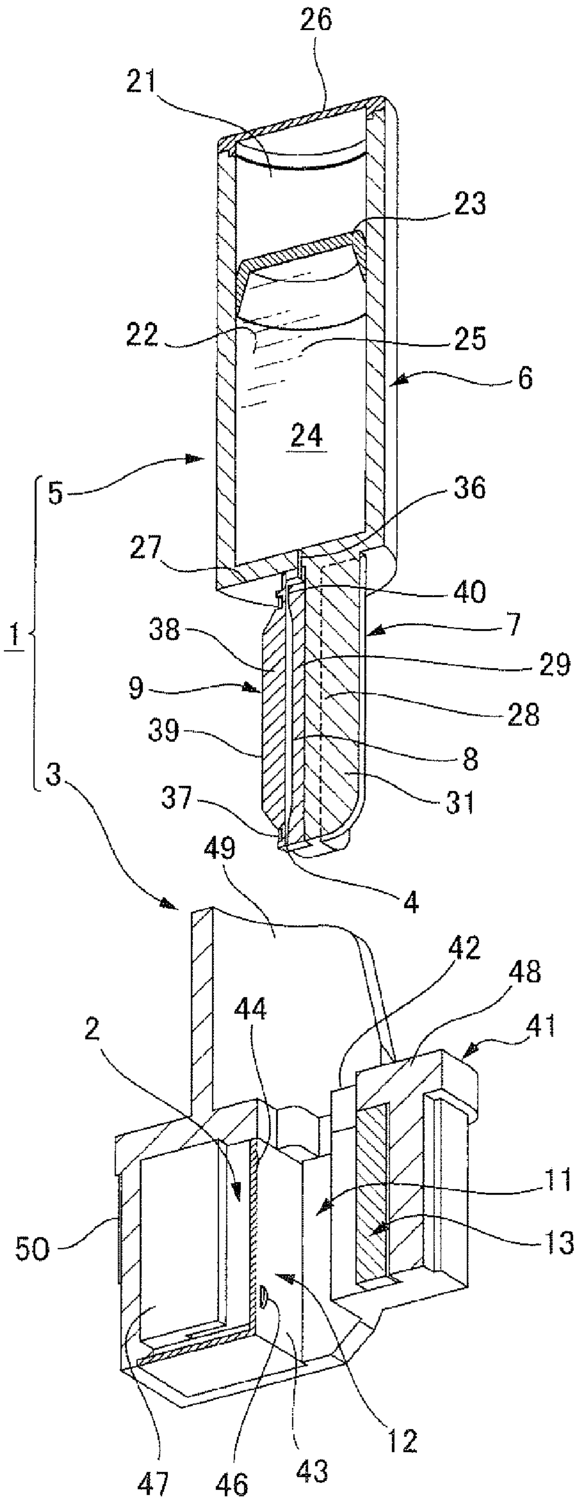
Figure 3B:
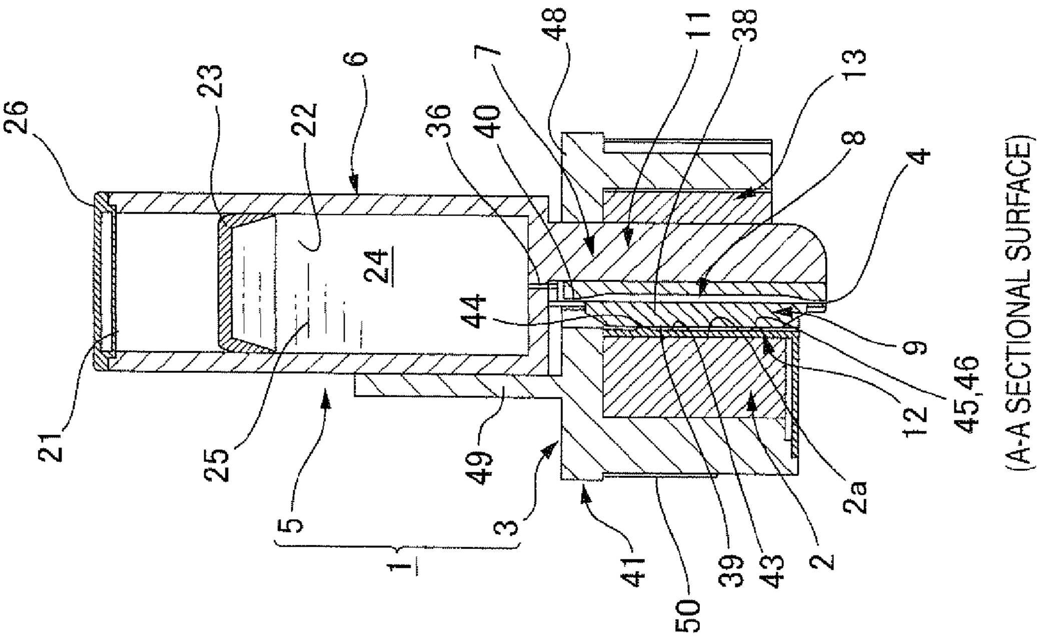
FIGS. 3A and 3B are a top view illustrating the liquid droplet ejecting head shown in FIGS. 1A and 1B and a longitudinal section view illustrating the liquid droplet ejecting head shown in FIGS. 1A and 1B, respectively.
Figure 3A:
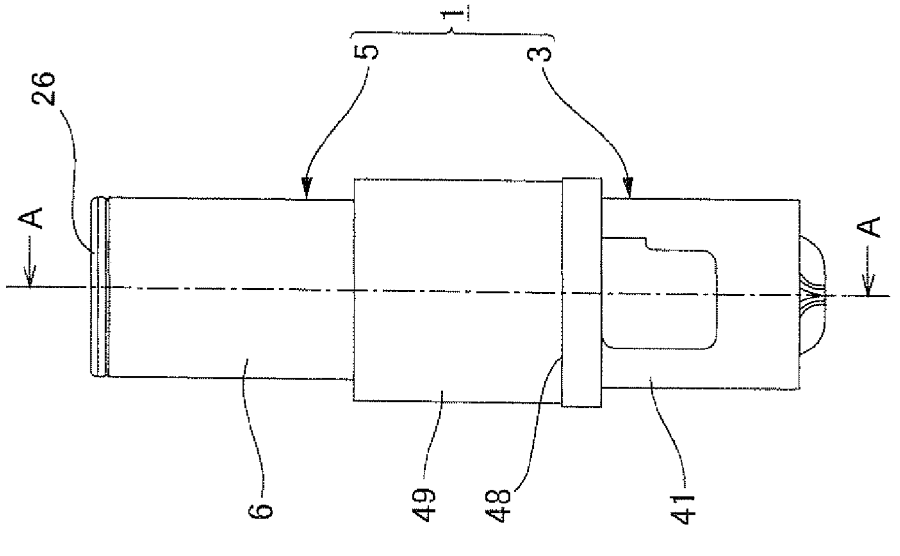

FIGS. 1A and 1B are perspective views illustrating a liquid droplet ejecting head. FIGS. 2A and 2B are a perspective view illustrating the detached liquid droplet ejecting head and a longitudinal sectional view illustrating the detached liquid droplet ejecting head, respectively. FIGS. 3A and 3B are a top view illustrating the liquid droplet ejecting head and a longitudinal section view illustrating the liquid droplet ejecting head, respectively. A major configuration of the liquid droplet ejecting head will be described with reference to these drawings. A liquid droplet ejecting head 1 includes a driving unit 3 having a piezoelectric element 2 therein and a nozzle unit 5 having a nozzle 4 for ejecting liquid droplets in a front end thereof. As shown in FIGS. 2A and 2B, the nozzle unit 5 is detachably connected to the driving unit 3.

The nozzle unit 5 includes a liquid container 6 with a cylindrical shape and a mount portion 7 protruding from a front end of the liquid container 6 so as to have a coaxial shape. The nozzle 4 is formed at the center of the front end surface of the mount portion 7, and a pressure generating passage 8 communicating with the nozzle 4 is formed in the mount portion 7. One side surface of the pressure generating passage 8 is constituted by a passage-side vibration plate 9 that is capable of vibrating in an out-of-plane direction.

The driving unit 3 includes a mount hole 11 in which the mount portion 7 is inserted so as to be detachably mounted. A part of an inner peripheral surface of the mount hole 11 is constituted by a driving-side vibration plate 12 that can vibrate in the out-of-plane direction. A piezoelectric element 2 constituted by a stacked piezo element is disposed in a rear surface of the driving-side vibration plate 12. When the piezoelectric element 2 is displaced, the driving-side vibration plate 12 vibrates. The inner surface of the mount hole 11 opposite the driving-side vibration plate 12 is constituted by an elastic member 13.

The driving-side vibration plate 12 is disposed in a position that comes in contact with the passage-side vibration plate 9 of the mount portion 7 of the nozzle unit 5 inserted into the mount hole 11. The elastic member 13 is elastically deformed to the outside of the mount hole 11 by the inserted mount portion 7 so that the mount portion 7 is urged toward the driving-side vibration plate 12 by an elastic restoring force. The mount portion 7 can be extracted from the mount hole 11 against an urging force of the elastic member 13. Accordingly, by extracting the mount portion 7, it is possible to detach the nozzle unit 5 from the driving unit 3 as shown in FIGS. 2A and 2B.

Figure 4:
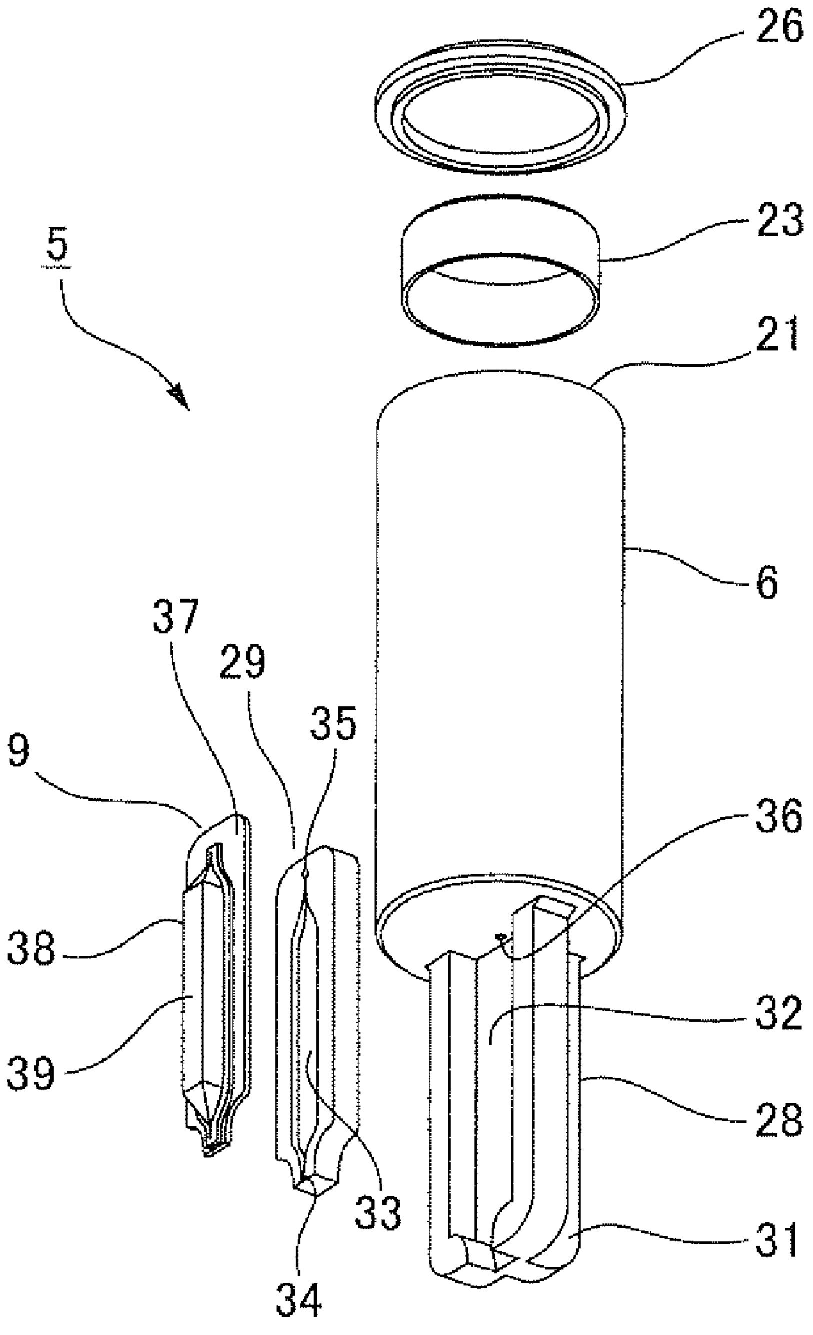
FIG. 4 is an exploded perspective view illustrating a nozzle unit of the liquid droplet ejecting head shown in FIGS. 1A and 1B.
Figure 5:
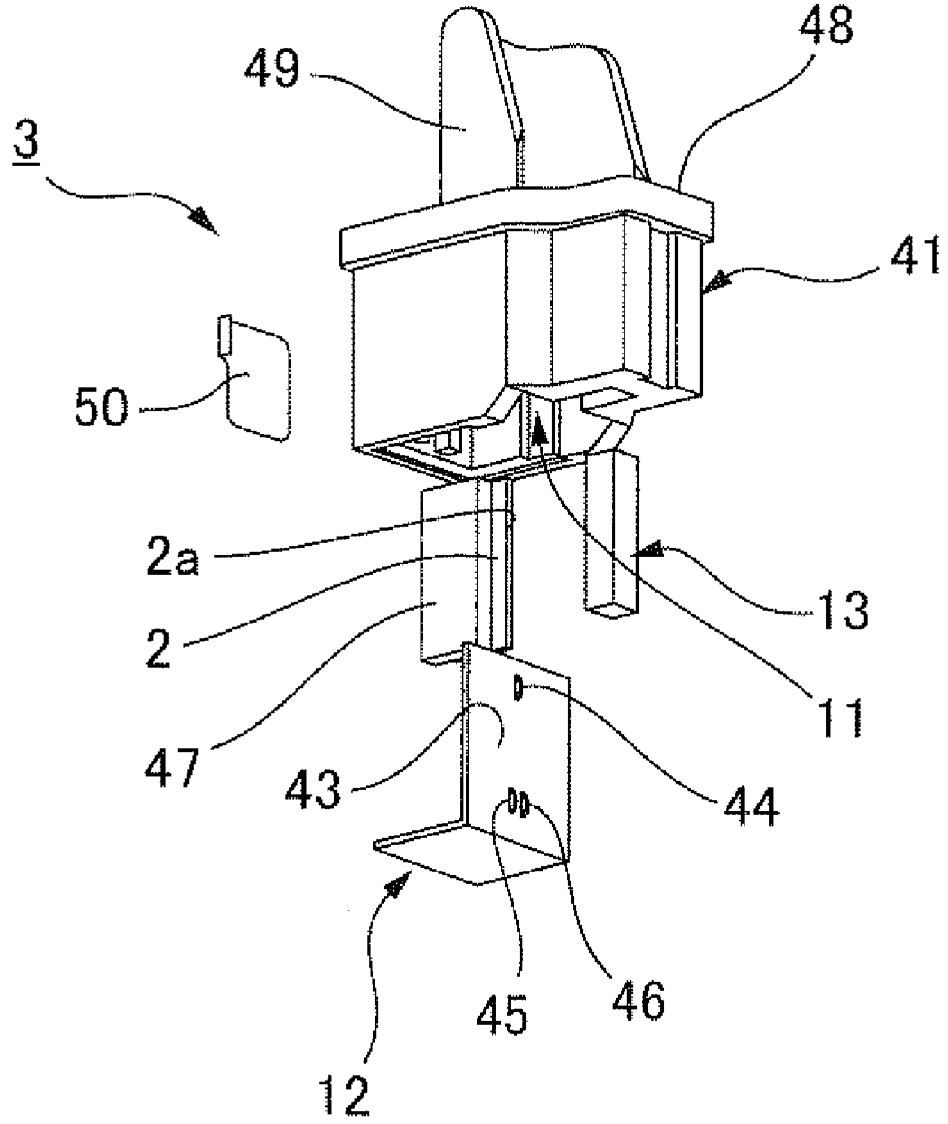
FIG. 5 is an exploded perspective view illustrating a driving unit of the liquid droplet ejecting head shown in FIGS. 1A and 1B.

FIG. 4 is an exploded perspective view illustrating the nozzle unit 5. FIG. 5 is an exploded perspective view illustrating the driving unit 3. Configurations of the nozzle unit 5 and the driving unit 3 will be described in detail with reference to these drawings.

The rear end of a liquid container 6 of the nozzle unit 5 is configured as an opening 21. In addition, the liquid container 6 includes a center hole portion 22 and a storing portion 24, which is in an air-tight state by a flat cup-shaped piston 23 inserted from the opening 21. The storing portion 24 is filled with liquids 25. The opening 21 is blocked by a cap 26, but is opened to open air between the cap 26 and the piston 23 through an air communication hole (not shown) formed in the cap 26. The piston 23 is configured to move toward a front end 27 of the liquid container 6 with consumption of the liquids 25 during the period when the liquids are stored liquid-tightly.

The mount portion 7 protrudes from a front end surface of the front end 27 of the liquid container 6 so as to have the coaxial shape. The mount portion 7 includes a protrusion plate 28 which has a fixed thickness and a fixed width and is incorporated into the liquid container 6, a passage board 29 which is mounted on the surface of the protrusion plate 28, and the passage-side vibration plate 9 which is attached to the surface of the passage board 29. In the protrusion plate 28, a protrusion claw 31 is incorporated that protrudes vertically from the center of the back surface. As shown in FIG. 4, a concave portion 32 for mounting the passage board 29 is formed on the surface of the protrusion plate 28. A passage groove 33 for forming the pressure generating passage 8 is formed on the surface of the passage board 29, and the front end of the passage groove 33 communicates with a nozzle groove 34 for forming the nozzle 4. A narrow communication groove 35 is formed in the back end of the passage groove 33, and the communication groove 35 communicates with a liquid supply hole 36 that is formed through the front end 27 of the liquid container 6 so as to be connected to the storing portion 24.

The passage-side vibration plate 9 that is attached to the surface of the passage board 29 has a thin outer peripheral portion 37 which has a contour shape corresponding to the passage board 29 and a thick center portion 38 which is surrounded by the outer peripheral portion 37. The center portion 38 is formed in an area which is smaller than the opened passage groove 33 by one size. The back surface of the passage board 29 is substantially flat, and the upper surface of the center portion 38 has a flat surface with a thin long rectangular shape. The flat surface is a contact surface 39 that comes in contact with the driving-side vibration plate 12.

By bonding the passage-side vibration plate 9 to the passage board 29, a communication passage 40 that communicates with the nozzle 4, the liquid passage 6, and the liquid supply hole 36 is formed therebetween.

A portion constituted by the liquid container 6 and the protrusion plate 28 of the nozzle unit 5, the passage board 29, and the passage-side vibration plate 9 can be formed of various materials such as stainless steel, glass, silicon, or plastic. When used for a disposable element, it is desirable that at least the part constituted by the liquid container 6 and the protrusion plate 28 is formed of an inexpensive plastic material.

Next, a structure of the driving unit 3 will be described. The driving unit 3 has a driving unit case 41 in which the cartridge mount hole 11 is formed. An opening 42 on an insertion side of the mount hole 11 in the driving unit case 41 has a mutually complementary shape with the contour shape of the mount portion 7 of the nozzle unit 5. In addition, a direction at the time of inserting the mount portion 7 into the mount hole 11 is defined by the complementary contour shape of the opening 42.

An inner peripheral portion of a connection hole opposite the passage-side vibration plate 9 in the mount portion 7 inserted into the mount hole 11 is defined by the driving-side vibration plate 12 attached to the driving unit case 41. The driving-side vibration plate 12 includes a flat opposite surface 43 opposed to the flat contact surface 39 of the passage-side vibration plate 9. One protrusion 44 is formed in the upper end within an area opposed to the contact surface in the opposite surface 43, and two protrusions 45 and 46 are formed in the lower end within the area. Moreover, three protrusions 44 to 46 come in contact with the contact surface 39 of the passage-side vibration plate 8.

The piezoelectric element 2 is disposed on the back surface of the opposite surface 43 of the driving-side vibration plate 12. The piezoelectric element 2 is attached to a fixing plate 47 made of a ceramic material or the like, and the fixing plate 47 is attached to the driving unit case 41. A displacement surface 2*a* of the piezoelectric element 2 is retained so as to come in contact with the back surface of the opposite surface 43 of the driving-side vibration plate 12. Accordingly, the driving-side vibration plate 12 vibrates with activation of the piezoelectric element 2.

Meanwhile, the thin long rectangular parallelepiped elastic member 13 is disposed in an inner peripheral surface opposite the driving-side vibration plate 12 in the mount hole 11, that is, a portion opposite the protrusion claw 31 in the mount portion 7. The surface of the elastic member 13 protrudes a little inwardly to the mount hole 11. In addition, the mount portion 7 is urged toward the driving-side vibration plate 12 on the opposite side by an elastically restoring force generated by the inserted protrusion claw 31 that deflects outwardly.

Consequently, the contact surface 39 of the passage-side vibration plate 9 of the mount portion 7 is pressed by the three protrusions 44 to 46 that are formed on the opposite surface 43 of the driving-side vibration plate 12 by a predetermined urging force. As a result, when the driving-side vibration plate 12 is vibrated by the piezoelectric element 2, the center portion with high rigidity in the passage-side vibration plate 8 vibrates, but is not bent. Accordingly, a volume of the pressure generating passage 8 increases or decreases, and thus an inner pressure thereof varies.

A supporting plate 49 that has a circular 180° arc shape protrudes from an end surface 48 in which the insertion-side opening 42 is formed in the driving unit case 41. Since an outer peripheral surface in the front end of the liquid container 6 in the nozzle unit 5 with the mount portion 7 inserted into the mount hole 11 is supported by the circular arc-shaped supporting plate 49, the nozzle unit 5 is prevented from being shaken. In addition, since a flexible cable 50 is attached to the side surface of the driving unit case 41, a driving voltage is supplied to an electrode of the piezoelectric element 2.

The driving unit case 41 can be formed of various materials such as stainless steel, glass, silicon, or plastic. In order to reduce a manufacturing cost, it is desirable that the driving unit case 41 is formed using an injection-molded case made of a plastic material.

In this way, when the mount portion 7 of the nozzle unit 5 is inserted into the mount hole 11 of the driving unit 3 in the liquid droplet ejecting device 1, the elastic member 13 is elastically deformed by the mount portion 7. Accordingly, the passage-side vibration plate 8 of the mount portion 7 is supported by the elastically restoring force of the elastic member 13 so as to come in contact with the three protrusions 44 to 46 of the driving-side vibration plate 12 on the side of the driving unit 3.

When the driving-side vibration plate 12 is vibrated by the piezoelectric element 2, the passage-side vibration plate 9 that comes in contact with the driving-side vibration plate 12 is also vibrated. That is, the flat center portion 38 with high rigidity vibrates in the out-of-plane direction, and thus the volume of the pressure generating passage 8 varies. Pulling and knocking by such vibration induce the liquid droplets to be ejected. For this reason, the piezoelectric element 2 is contracted. In this way, the driving-side vibration plate 12 is displaced backward from the passage-side vibration plate 9. Since the passage-side vibration plate 9 is pressed against the driving-side vibration plate 12, the passage-side vibration plate 9 follows the driving-side vibration plate 12, and then is displaced to the driving-side vibration plate 12. As a result, the volume of the pressure generating passage 8 temporarily increases. Afterward, the piezoelectric element 2 is lengthened, and then the passage-side vibration plate 9 is again pressed. Accordingly, the volume of the pressure generating passage 8 decreases, thereby temporarily increasing the inner pressure thereof. In this way, the liquid droplets are ejected from the nozzle 4.

In this case, the mount portion 7 of the nozzle unit 5 is retained by the elastically restoring force of the elastic member 13. In addition, just by simply extracting the mount portion 7 from the mount hole 11 against the urging force generated by the elastically restoring force, the nozzle unit 5 can be detached from the driving unit 3. Accordingly, when the nozzle 4 is clogged, the nozzle unit 5 can be separately exchanged. Moreover, since the expensive driving unit 3 equipped with the piezoelectric element 2 continues to be used, it is more cost efficient.

In particular, when the liquid droplet ejecting head 1 is used to supply chemical liquids or the like in a field such as a clinical care, the nozzle unit 5 may be separately exchanged to exchange the chemical liquids or the like. Accordingly, since it is not required that all components of the liquid droplet ejecting head 1 be disposable, the liquid droplet ejecting head 1 is considerably economical.

As described above, the liquid droplet ejecting head 1 according to the embodiment has a structure in which the nozzle unit 5 having the nozzle 4 can be detached from the driving unit 3 equipped with the piezoelectric element 2. Accordingly, when the nozzle 4 of the nozzle unit 5, which is used as the disposable unit, is clogged, the nozzle unit 5 can be separately exchanged. As a result, the expensive driving unit 3 equipped with the piezoelectric element 2 can continue to be used.

Accordingly, the above-described assembly is less expensive than an assembly where all components of the liquid droplet ejecting head must be exchanged when the nozzle 4 is clogged. It is possible to reduce the number of head maintenance operations performed to prevent the nozzle from being clogged, thereby reducing an amount of unnecessarily consumed liquid. Furthermore, the above-described liquid droplet ejecting head is suited for disposable liquid droplet ejecting heads for supplying chemical liquids, test liquids, or the like.

(Multiple Liquid Droplet Ejecting Head)

Figure 6:
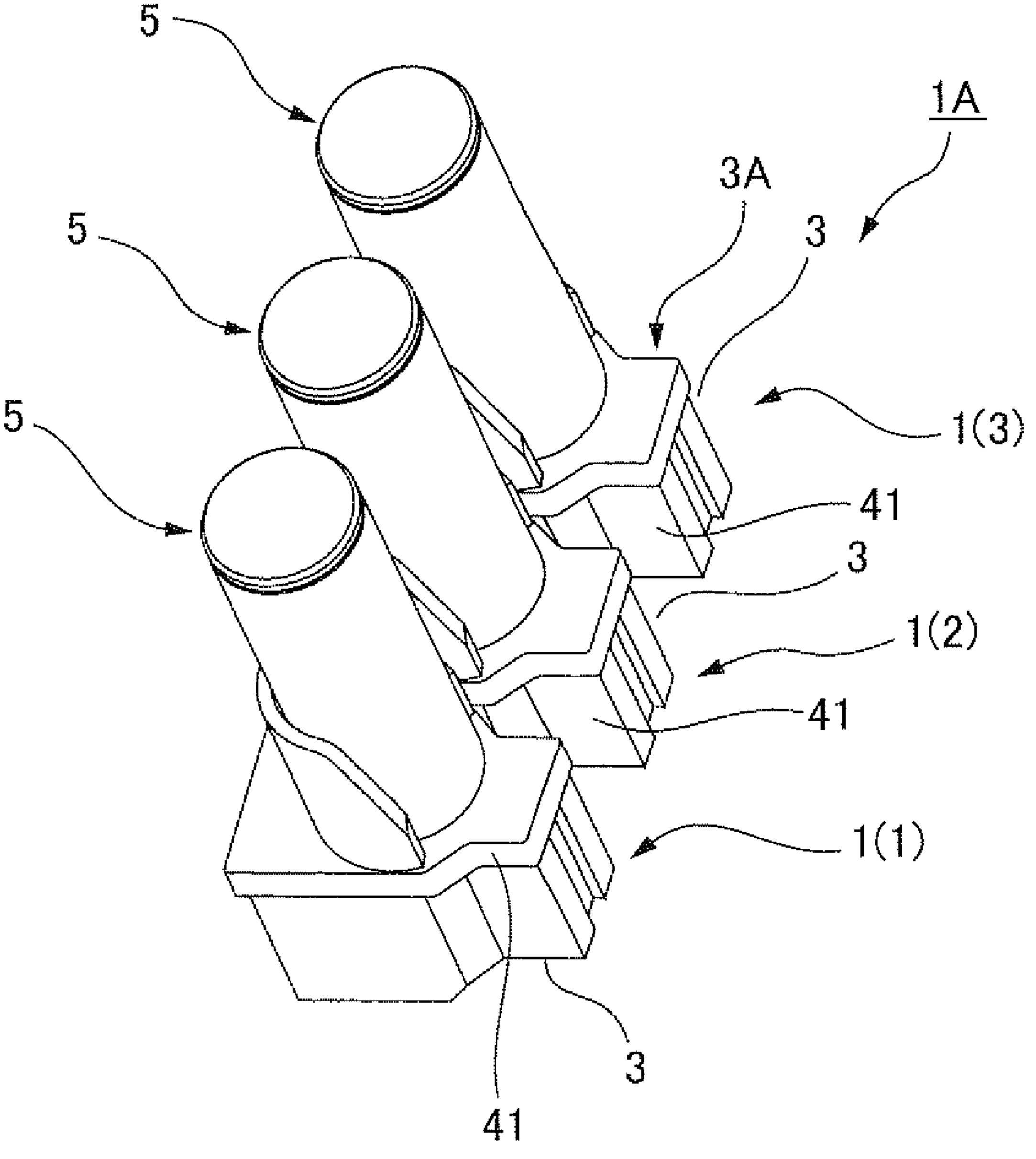
FIG. 6 is a perspective view illustrating a multiple liquid droplet ejecting head.

Next, FIG. 6 is a perspective view illustrating a multiple liquid droplet ejecting head. A multiple liquid droplet ejecting head 1A shown in FIG. 6 has a structure in which three liquid droplet ejecting heads 1(1) to 1(3) are linked with each other. The structure of each of the liquid droplet ejecting heads 1(1) to 1(3) is the same as that of the liquid droplet ejecting head 1 shown in FIGS. 1 to 5. Accordingly, the same reference numerals are given to the corresponding constituents. In the example, the side surfaces of the driving unit cases 41 of the liquid droplet ejecting heads 1(1) to 1(3), and thus a multiple driving unit 3A is formed.

In addition, the three liquid droplet ejecting heads are linked in FIG. 6, but the number of the liquid droplet ejecting heads may be 2, 4 or more. Moreover, the liquid droplet ejecting heads may not be shaped in a row.

When any one of the liquid droplet ejecting heads is clogged in the multiple liquid droplet ejecting head, only the nozzle unit of the clogged liquid droplet ejecting head is required to be exchanged. Moreover, there is an advantage in that different types of chemical liquids, test liquids, or the like can be simultaneously supplied by the liquid droplet ejecting head.

Second Embodiment

Clinical Inspection Device

Figure 7:
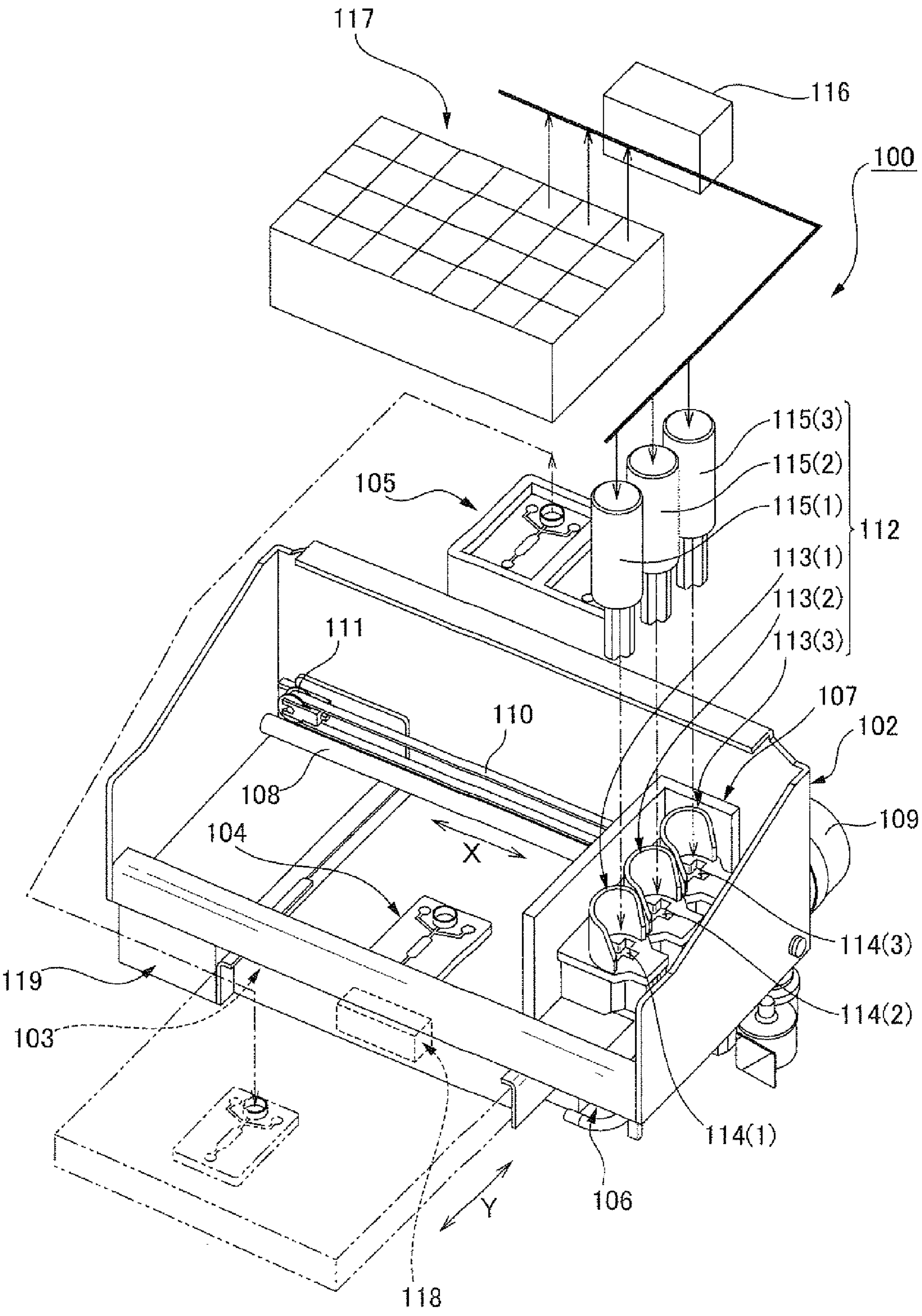
FIG. 7 is a schematic configuration diagram illustrating major constituents of a clinical inspection device.

FIG. 7 is a schematic configuration diagram illustrating major constituents of a clinical inspection device using the three liquid droplet ejecting heads 1 shown in FIG. 6 as a dispenser.

A clinical inspection device 100 includes an inspection table 103 which is attached to the center portion of a bottom surface of a device frame 102 with a rectangular frame and can be taken out and put in front and back directions (a Y direction). One piece of an inspection chip 104 that is supplied in advance is placed in the inspection table 103. The inspection chip 104 is housed in a chip magazine 105 attached to the back center portion of the device frame 102. The inspection chip 104 housed in the chip magazine 105 is conveyed in the front direction of the device along a conveyance path indicated by a dashed line by a chip conveyance mechanism (not shown) so as to be loaded in the inspection table 103 that is extracted frontward as shown in an imaginary line.

In the side of the inspection table 103, a maintenance unit 106 is arranged in the bottom surface of the device frame 102. Above the inspection table 103 and the maintenance unit 106, a carriage 107 is arranged so as to move in right and left directions (an X direction). The carriage 107 moves in the X direction along a carriage guide shaft 108, which is suspended in a width direction of the device frame 102 by a carriage driving mechanism constituted by a carriage motor 109, a timing belt 110, a pulley 111, etc.

A dispenser 112 of an ink jet type is mounted on the carriage 107. The dispenser 112 is constituted by three liquid droplet ejecting heads. That is, the dispenser 112 includes three driving units 113(1) to 113(3) mounted on the carriage 107 and three nozzle units 115(1) to 115(3) detachably mounted on three mount holes 114(1) to 114(3) formed in the three driving units 113(1) to 113(3), respectively.

The nozzle unit 115(1) is a nozzle unit for a buffer chemical, the nozzle unit 115(2) is a nozzle unit for a reaction chemical, and the nozzle unit 115(3) is a nozzle unit for an index chemical. Liquid structures of each of the cartridge mount portions and each of the nozzle units are the same as those in the liquid droplet nozzle 1 shown in FIGS. 1 to 5. Accordingly, the description will be omitted.

The nozzle units 115(1) to 115(3) are supplied from a magazine 117 for housing several nozzle units storing various types of the test reagents to the driving unit 113(1) to 113(3) along a conveyance path indicated by thick lines by a cartridge conveyance mechanism 117.

An optical measurement unit 118 described below is built in a lower surface in which the inspection chip 104 is loaded in the inspection table 103. In addition, in the side of the inspection table 103, a liquid sending pump unit 119 is attached to the bottom surface of the device frame 102.

Figure 8A:
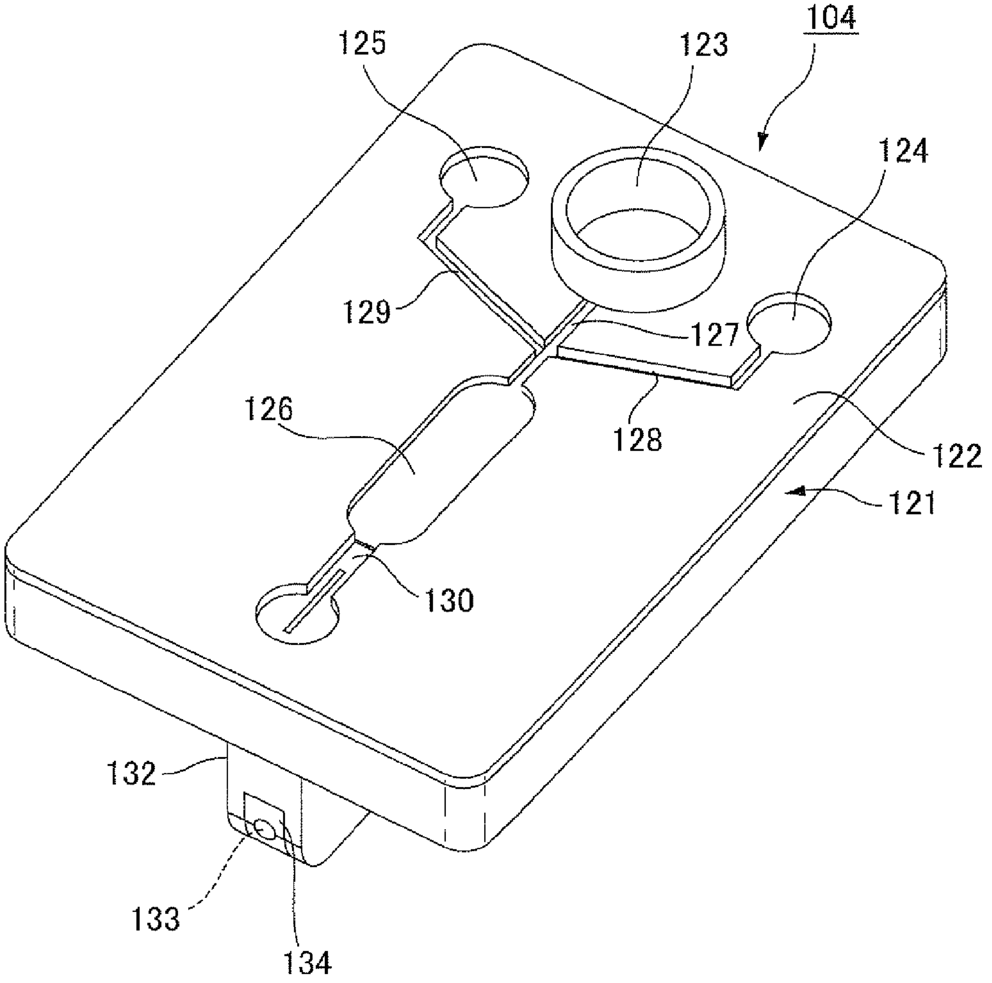
FIGS. 8A and 8B are a perspective view illustrating an inspection chip and a partial sectional view illustrating the inspection chip mounted in an inspection table, respectively.
Figure 8B:
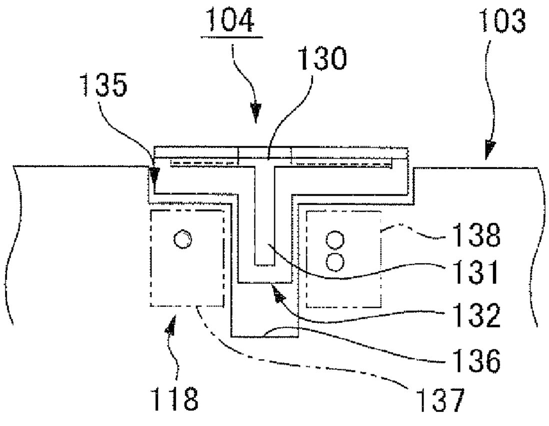
Figure 9C:
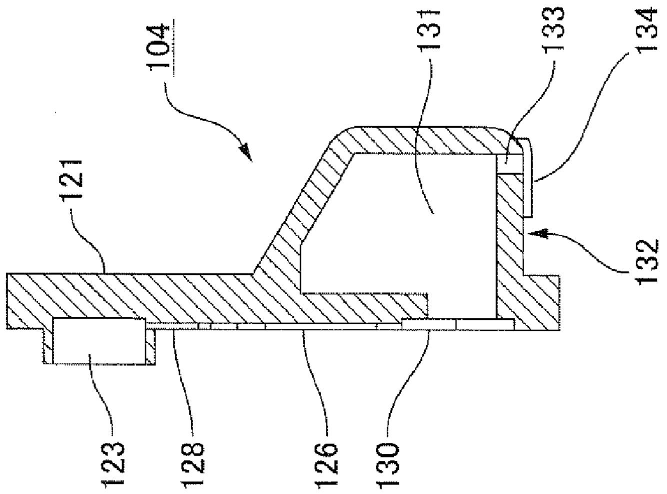
FIGS. 9A, 9B, and 9C are a top view illustrating the inspection chip, a front view illustrating the inspection chip, and a sectional view illustrating the inspection chip, respectively.
Figure 9A:
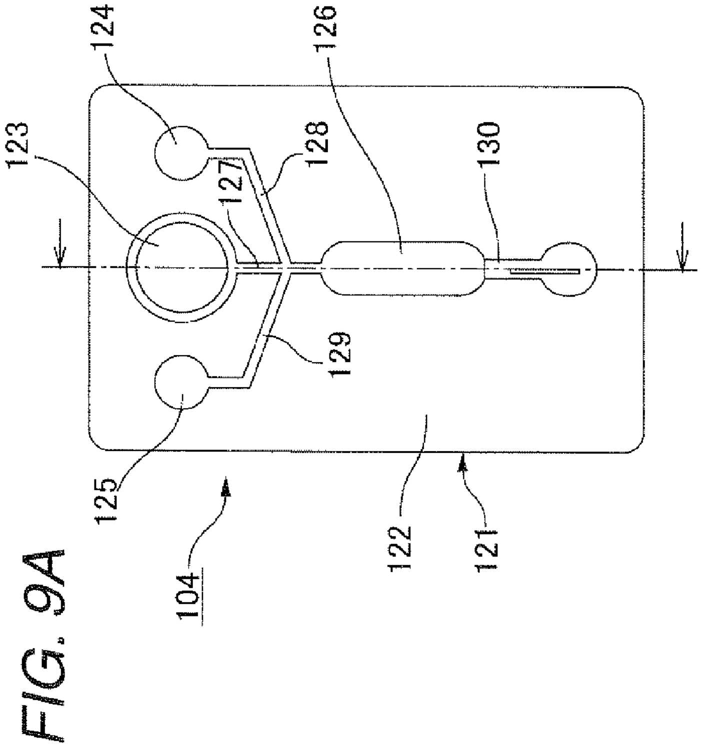
Figure 9B:
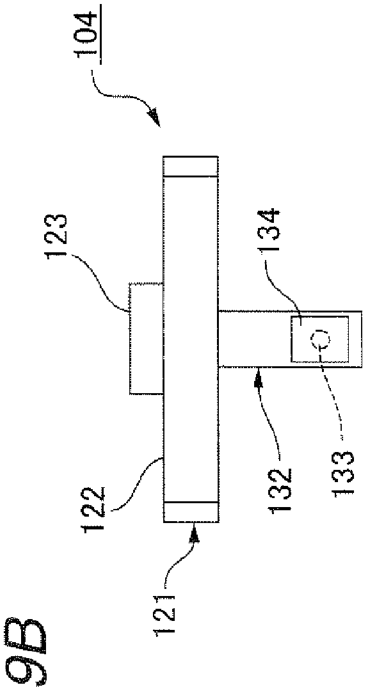

FIGS. 8A and 8B are a perspective view illustrating the inspection chip 104 and a schematic sectional view illustrating the inspection chip 104 loaded in the inspection table 103, respectively. FIGS. 9A, 9B, and 9C are a top view illustrating the inspection chip 104, a front view illustrating the inspection chip 104, and a sectional view illustrating the inspection chip 104, respectively. The inspection chip 104 includes a board 121 with a flat rectangular shape. An introduction hole 123 for a round inspection object and the buffer chemical, an introduction hole 124 for a round index chemical, an introduction hole 125 for a round reaction chemical, and an oval reaction chamber 126 are formed on a flat surface 122 of the board 121. Communication grooves 127, 128, and 129 are communicated with the introduction holes 123, 124, and 125. The communication grooves 127, 128 and 129 are joined together so as to be connected to the reaction chamber 126. The reaction chamber 126 is connected to a measurement cell 131 through a communication groove 130.

The buffer chemical, the index chemical, and the reaction chemical are dispensed to the introduction holes 123, 124, and 125 of the inspection chip 104 loaded in the inspection table 103, respectively, by the dispenser 112. The dispensed chemical liquids are moved along each of the communication grooves 127, 128, and 129 to the reaction chamber 126 by a capillary force. The inspection object (for example, blood plasma) that is moved to the reaction chamber 126 along with the buffer chemical is reacted with the reaction chemical.

The measurement cell 131 is a small passage that is formed in an optically transparent protrusion plate 132 protruding vertically from the back surface of the board 121. The measurement cell 131 communicates with a connection hole 133 opened to the sectional surface of the protrusion plate 132. The connection hole 133 is blocked by a film 134 that has air permeable and liquid impermeable characteristics. For example, as the film 134, a GORE-TEX® material can be used.

As shown in FIG. 8B, a concave portion 135 for mounting the inspection chip 104 is formed in the upper surface of the inspection table 103, and a groove 136 for inserting the protrusion plate 132 of the inspection chip 104 is formed in the center of the bottom of the concave portion 135. The optical measurement unit 118 is arranged in the inspection table 103 and is equipped with a white laser light source 137 and a light-receiving portion 138 which are arranged in both sides of the groove 136. For example, the measurement unit 118 is an absorption spectrometer.

When the inspection chip 104 is mounted on the inspection table 103, the connection hole 133 communicating with the measurement cell 131 of the inspection chip 104 is connected to a suction port (not shown) of the liquid sending pump unit 119 through the film 134. When the liquid sending pump unit 119 is driven, the measurement cell 131 becomes in a negative pressure state. At this time, the inspection object and the chemical liquids gather in the reaction charter 126 that communicates with the measurement cell 131 through the communication groove 130. The measurement unit 118 detects the state of the introduced inspection object by absorbance.

Figure 10A:
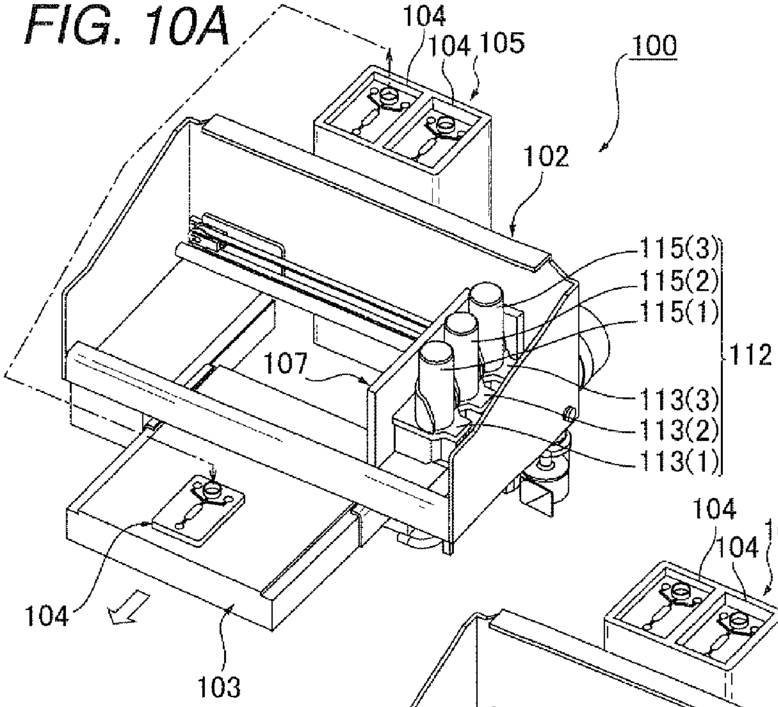
FIGS. 10A, 10B, and 10C are diagrams for explaining an operation of the clinical inspection device shown in FIG. 7.
Figure 10B:
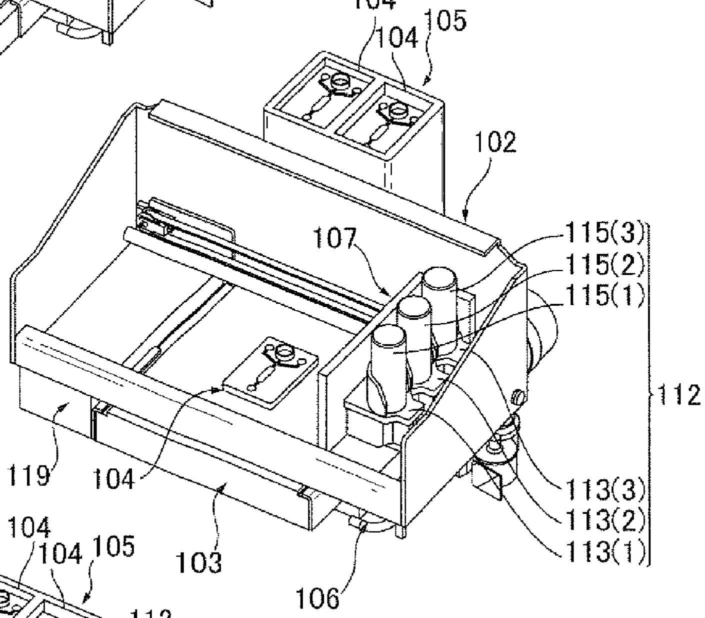
Figure 10C:
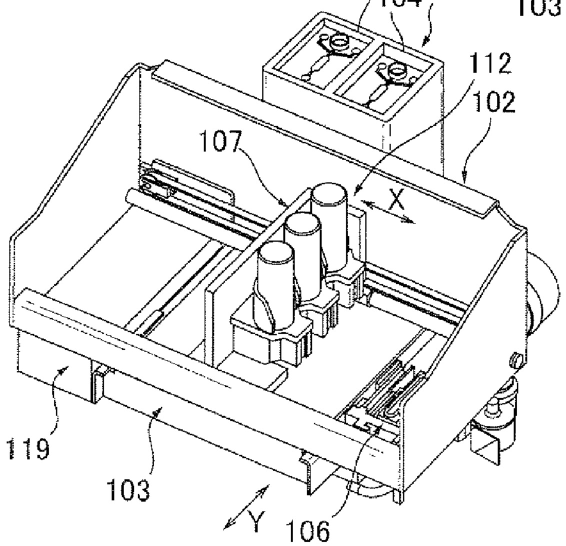

FIGS. 10A, 10B, and 10C are diagrams for explaining an operation of the clinical inspection device 100. The inspection operation of the clinical inspection device 100 will be described with reference with FIGS. 7 and 10A to 10C.

First, as shown in FIG. 7, the inspection chip 104 to which the inspection object (for example, blood plasma) is supplied is mounted on the chip magazine 105 of the clinical inspection device 100. Next, the three nozzle units 115(1) to 115(3) storing the buffer chemical, the index chemical, and the reaction chemical, respectively, are extracted from the magazine 117 to mount the mount holes 114(1) to 114(3) of the three driving units 113(1) to 113(3), respectively.

Next, as shown in FIG. 10A, the inspection table 103 is extracted frontward, and the inspection chip 104 is detached from the chip magazine 105 to be mounted on the upper surface of the inspection table 103.

After inspection, the inspection table 103 returns to the original position as shown in FIG. 10B.

Afterward, as shown in FIG. 10C, the dispenser 112 is moved in the X direction by the carriage 107, and then is positioned right above the inspection chip 104 of the inspection table 103. For example, when the dispenser 112 is positioned right above the inspection chip 104, the nozzle of the nozzle unit 115(3) for the index chemical of the dispenser 112 is positioned right above the introduction hole 124 for the index chemical of the inspection chip 104. In this case, the piezoelectric element of the driving unit 113(3) is driven to eject and dispense the index chemical to the introduction hole 124.

Next, the inspection table 103 is moved a little in the Y direction (the front and back directions), and the carriage 107 is moved a little in the X direction (the right and left directions), so that the nozzle of the nozzle unit 115(1) for the buffer chemical is positioned right above the introduction hole 123 of the inspection chip 104, for example.

Subsequently, the buffer chemical is ejected and dispensed to the introduction hole 123. In the same manner, the reaction chemical is dispensed to the remaining introduction hole 125. In this way, since the chemical liquids are dispensed by using the dispenser 112 of an ink jet type, it is possible to dispense a small amount of chemical with a high precision.

After the dispensing operation ends, the carriage 107 returns to the standby position opposite the maintenance unit 106. The maintenance unit 106 has a function of preventing dryness, attachment of foreign substances, and mixture of foreign substances of the nozzles of the nozzle unit 115(1) to 115(3), like a maintenance unit of an ink jet head of an ink jet printer.

Subsequently, the chemical liquids dispensed to the inspection chip 104 are moved along the communication grooves 127 to 129 to the reaction chamber 126 by a capillary force. In addition, the inspection object (for example, blood plasma) which is moved to the reaction chamber 126 along with the buffer chemical is reacted with the reaction chemical. With a predetermined time lapsed, the liquid sending pump unit 119 is driven so that the measurement cell 131 of the inspection chip 104 communicating with the suction port becomes in a negative pressure state. As a result, the chemical including the inspection object is introduced from the reaction chamber 126 to the measurement cell 131. In the embodiment, the absorbance representing a reaction state of the introduced inspection object is measured by the measurement unit 118 included in the inspection table 13.

In this case, when the inspection object is inspected by using different types of the chemical or the like, different cartridges can be exchanged by extracting the nozzle units 115(1) to 115(3). As a result, cleaning or the like of the dispenser 112 is not required.

In addition, when the nozzle unit 115 is empty, the nozzle unit 115 is discarded. In this case, since an actuator (the piezoelectric element) is not mounted on the nozzle unit 115, it is possible to manufacture the nozzle unit 115 at a low cost. Moreover, even though the nozzle unit 115 is disposable, cost efficiency is not deteriorated.

In this embodiment, the dispenser 112 of an ink jet type is used to dispense the chemical liquids such as the index chemical or the reaction chemical. It is also possible to dispense the inspection object to the inspection chip 104 using the same dispenser. In addition, the dispenser 112 is shown with three liquid droplet ejecting heads; however, one, two, four, or more liquid droplet ejecting heads may be used.

In this embodiment, the dispenser is applied to a clinical inspection device, but may be applied to other inspection devices other than the described clinical inspection device. For example, examples of an inspection device for precisely injecting a fixed amount of sample or test reagent include a gas chromatography, a high performance liquid chromatography (HPLC), and the like, to which the liquid droplet ejecting head described herein may be applied.

As described above, the clinical inspection device according the embodiment use the same mechanism as the ink jet head for the dispenser for dispensing the test liquid or the inspection object. Moreover, in the nozzle units housing the test liquids or the inspection object that are disposable, only the ejecting head and the ejecting pressure generating passage are formed, so that the actuator such as the piezoelectric element is arranged in the cartridge mount portion.

Accordingly, it is possible to manage a small amount of test liquid or the inspection object that are dispensed with high precision, thereby inspecting the inspection object with high precision. Moreover, when the test liquid or the inspection object is exchanged to be inspected, only the nozzle unit is exchanged with a nozzle unit housing another test liquid or inspection object, by extracting the nozzle unit from the nozzle unit mounting portion. In addition, cleaning or the like, which is required in a known dispenser to clean passages of the test liquid or the inspection object of the dispenser, is not required. Since the actuator is not mounted on the disposable nozzle unit, it is possible to reduce a manufacturing cost and a running cost. Moreover, since the actuator is not configured to come in contact, durability is excellent.

Third Embodiment

Clinical Inspection Device

Figure 11:
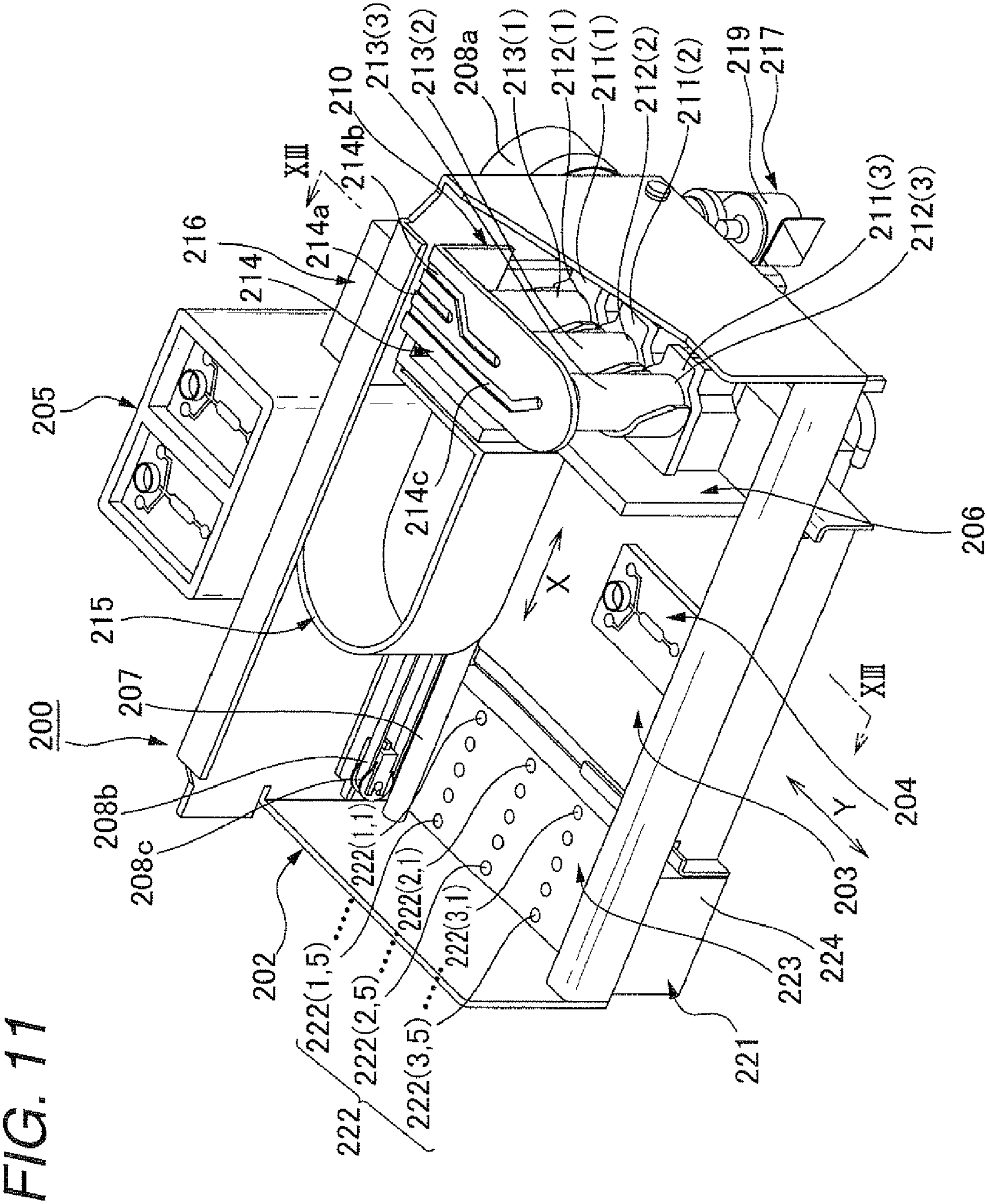
FIG. 11 is a schematic configuration diagram illustrating major constituents of a clinical inspection device.
Figure 12:
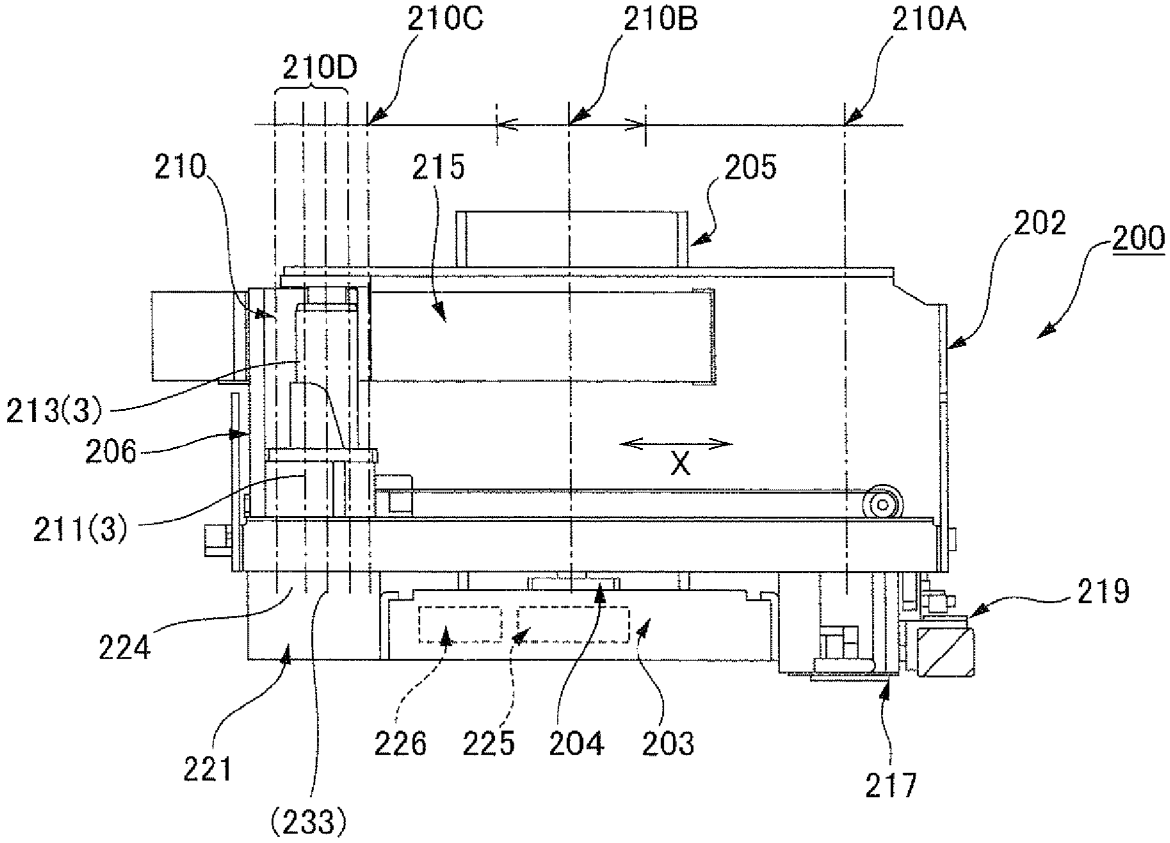
FIG. 12 is a front view illustrating the clinical inspection device shown in FIG. 11.
Figure 13:
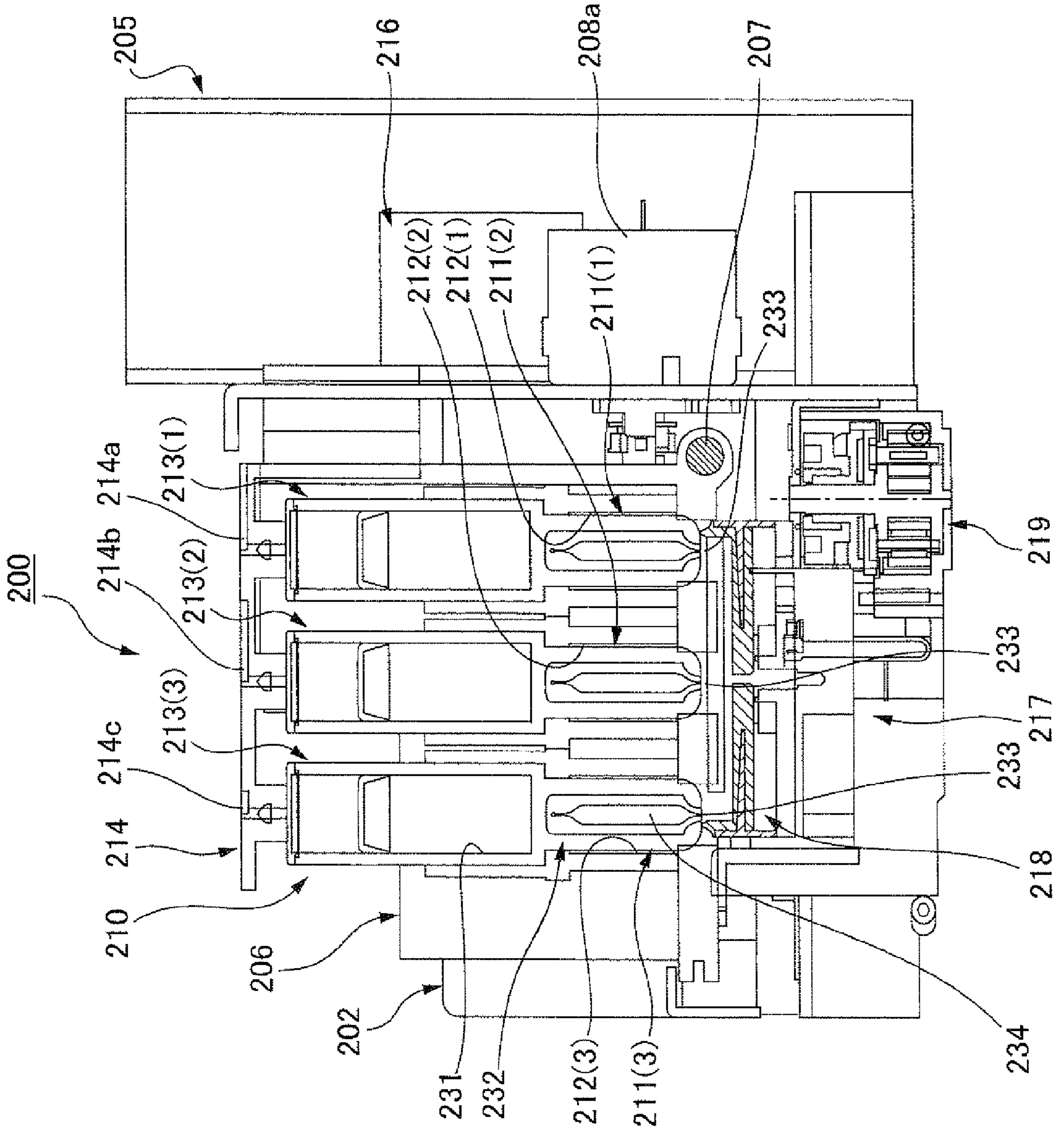
FIG. 13 is a sectional view illustrating the clinical inspection device taken along the line XIII-XIII shown in FIG. 11.

FIG. 11 is a schematic configuration diagram illustrating major constituents of a clinical inspection device according to a third embodiment. FIG. 12 is a front view illustrating the clinical inspection device. FIG. 13 is a schematic sectional view illustrating the clinical inspection device taken along the line XIII-XIII shown in FIG. 11. In the clinical inspection device according to the third embodiment, the three liquid droplet ejecting heads shown in FIG. 6 are also used for a dispenser.

A clinical inspection device 200 includes an inspection table 203 which is attached to the center portion of a bottom surface of a device frame 202 with a rectangular frame and can be taken out and put in front and back directions (a Y direction). One piece of an inspection chip 204 that is supplied in advance is placed in the inspection table 203. The inspection chip 204 is housed in a chip magazine 205 attached to the back center portion of the device frame 202.

The inspection chip 204 is the same as the inspection chip 104 according to the second embodiment shown in FIGS. 8A, 8B, and 9A to 9C. Accordingly, the description will be omitted. In addition, when constituents of the inspection chip 204 are described below, the same reference numerals are given to the corresponding constituents of the inspection chip 104.

A head carriage 206 that can reciprocate in right and left directions (an X direction) via the upper portion of the inspection table 203 is attached in the device frame 202. The head carriage 206 moves in the X direction along a carriage guide shaft 207, which is suspended in the X direction by a carriage driving mechanism constituted by a carriage motor 208*a*, a timing belt 208*b*, a pulley 208*c*, etc. The liquid droplet ejecting head 210 that dispenses chemical liquids for inspecting an inspection object to the inspection chip 204 is mounted on the head carriage 206.

The liquid droplet ejecting head 210 includes three driving units 211(1) to 211(3) mounted on the head carriage 206 and three nozzle units 213(1) to 213(3) detachably mounted in mount holes 212(1) to 212(3) of the driving units 211(1) to 211(3) from an upper side, respectively.

As shown in FIG. 13, an upper portion and a lower portion of each of the nozzle units 213(1) to 213(3) serve as a storing portion 231 for storing chemical liquids and a mount portion 232 for being mounted on each of the mount holes 212(1) to 212(3), respectively. Nozzles 233 for ejecting liquid droplets are formed in the front ends of the mount portions 232. Accordingly, pressure generating passages 234 for varying a pressure required to eject the liquid droplets from the nozzles 233 are formed in the insides of the mount portions 232. Opposite ends of each of the pressure generating passages 234 communicate with the corresponding nozzle 233 and the corresponding storing portion 231, respectively.

The liquid droplet ejecting head constituted by the nozzle units and the driving units is the same as the liquid droplet ejecting head 1 shown in FIGS. 1 to 5. Accordingly, the detailed description will be omitted.

Next, as shown in FIGS. 11 and 13, a suction passage plate 214 is detachably mounted on the head carriage 206 so as to cover the three nozzle units 213(1) to 213(3). Suction passages 214*a* to 214*c* that communicate with the storing portions 231 of the nozzle units 213(1) to 213(3) blocked by a film (not shown) are formed in the upper surface of the suction passage plate 214. As shown in FIG. 13, one end of each of the suction passages 214*a* to 214*c* communicates with each inner portion of the storing portions 231 of the nozzle units 213(1) to 213(3). The other end of each of the suction passages 214*a* to 214*c* is connected to a suction port (not shown) of a head suction pump 216 mounted on the back surface of the device frame 202 through a flexible suction tube (not shown) extracted along a flexible wiring plate 215 that is curved in a U shape between the head carriage 206 and the device frame 202.

A three-way electromagnetic valve (not shown) is disposed between the suction tube and the suction port. A three-way electromagnetic plate can be switched so that liquids of the nozzle units 213(1) to 213(3) are sucked by using the head suction pump 216. In addition, a middle portion between the nozzle units 213(1) to 213(3) and the head suction pump 216 can be cut so that the storing portions 231 of the nozzle units 213(1) to 213(3) are opened to open air.

A waste liquid recovery unit 217 is disposed on one side of the inspection table 203 of the bottom surface of the device frame 202. The waste liquid recovery unit 217 includes caps 218 for covering the front ends of the nozzles 233 of the nozzle units 213(1) to 213(3), a waste liquid recovery pump 219 such as a tube pump, and a waste liquid recovery portion (not shown) of the waste liquids sucked by the waste liquid recovery pump 219. The caps 218 cover the front ends of the nozzle units 213(1) to 213(3), and the waste liquid recovery pump 219 is driven so that the liquids of the nozzle units 213(1) to 213(3) can be extracted outward through the nozzles 233 to be recovered.

A liquid storing unit 221 is disposed on the other side of the inspection table 203 adjacent the bottom surface of the device frame 202. The liquid storing unit 221 includes a well plate 223 in which wells 222 for storing liquids are formed in a matrix shape and an elevation unit 224 elevating the well plate 223. For example, the wells 222(1, 1) to 222(3, 5) of three rows and five columns are formed. In addition, the row interval can be configured so as to correspond to the nozzles 233 of the three nozzle units 213(1) to 213(3).

That is, the three wells 222(1, 1) to 222(3, 1) of a first row are cleaning liquid storing portions for storing cleaning liquids. The remaining wells are chemical liquid storing portions. That is, the four wells 222(1, 2) to 222(1, 5) of a first column are storing portions for storing test reagents (index chemical liquids). The four wells 222(2, 2) to 222(2, 5) of a second column are storing portions for storing reaction chemical liquids. The four wells 222(3, 2) to 222(3, 5) of a third column are storing portions for storing buffer chemical liquids.

As denoted by a broken line in FIG. 12, an analysis unit 225 for measuring or analyzing a reaction result about the inspection object in the inspection chip 204 is disposed below a position in which the inspection chip 204 is placed in the inspection table 203. The analysis unit 225 also includes a liquid sending pump unit 226.

With reference to FIG. 12, a movement position of the liquid droplet ejecting head 210 mounted on the head carriage 206 will be described. The nozzles 233 of the liquid droplet ejecting head 210 are configured to be conveyed along a head movement path via a standby position 210A opposite the waste liquid recovery unit 217, a dispensation position 210B (liquid droplet-ejected position) opposite the inspection chip 204 on the inspection table 203, a cleaning liquid suction position 210C opposite the wells 222(1, 1) to 222(3, 1) for storing cleaning liquid in the liquid storing portion 221, and a suction position 210D for sucking the chemical liquids of the four positions opposite the wells of each row other than the above-described wells. FIG. 12 shows that the nozzles 233 of the liquid droplet ejecting head 210 are positioned in the wells 222(1, 3) to 222(3, 3) of the third row. FIG. 11 shows the liquid droplet ejecting head 210 positioned in the standby position 210A.

FIGS. 14 and 15 are diagrams for explaining an operation of the clinical inspection device 200, and particularly an operation of dispensing the chemical liquids.

As shown in FIGS. 11 and 13, the empty nozzle units 213(1) to 213(3) are positioned in the mount holes 212(1) to 212(3) of the driving units 211(1) to 211(3) mounted on the head carriage 206 that is in the standby position 210A, respectively. In addition, the suction passage plate 214 is attached above the nozzle units 213(1) to 213(3).

Figure 14A:
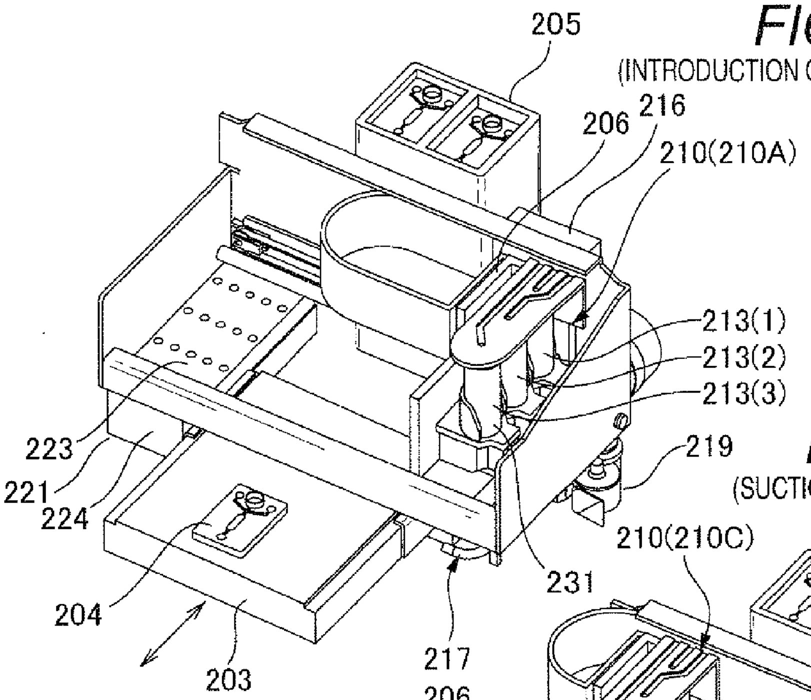
FIGS. 14A, 14B, and 14C are diagrams for explaining a dispensation operation of the clinical inspection device shown in FIG. 11.
Figure 14B:
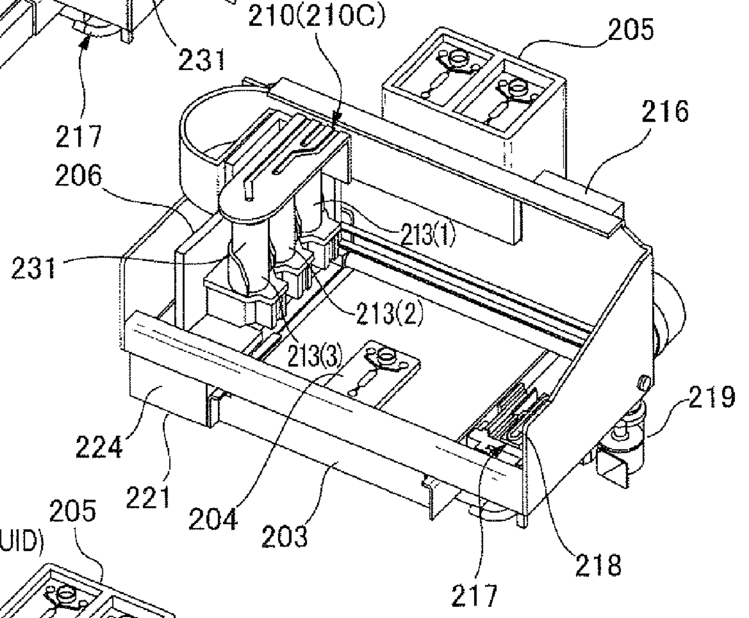

Subsequently, as shown in FIG. 14A, the inspection table 203 is taken out frontward to load the inspection chip 204 extracted from the chip magazine 205 in a position which is determined in advance in the inspection table 203. After the inspection chip 204 is loaded, the inspection table 203 is returned to the original position. Afterward, as shown in FIG. 14B, the liquid droplet ejecting head 210 is moved to the cleaning liquid suction position 210C by the head carriage 206. In the cleaning liquid suction position 210C, the well plate 233 is elevated by the elevation unit 224, and then the front ends of the nozzles 233 of the nozzle units 213(1) to 213(3) are put in the cleaning liquids stored in the wells 222(1, 1) to 222(3, 1) that form the cleaning liquid storing portions. In this state, the head suction pump 216 is driven so that the storing portions 231 of the nozzle units 213(1) to 213(3) become in a negative pressure state. In this way, the cleaning liquids are sucked to the storing portions 231 of the nozzle unit 213(1) to 213(3).

Figure 14C:
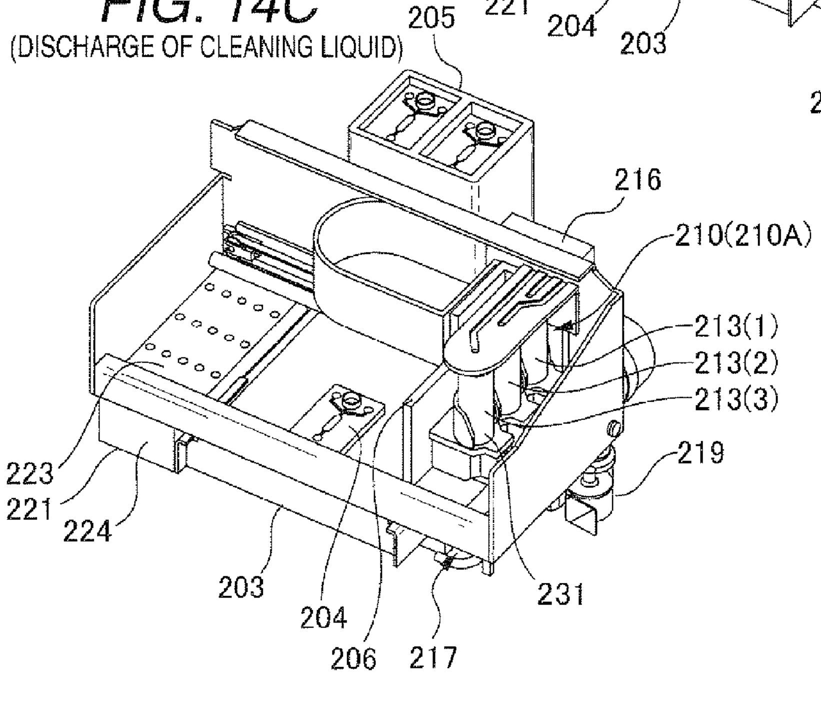

Subsequently, as shown in FIG. 14C, the liquid droplet ejecting head 210 is returned to the standby position 210A by the head carriage 206, and then a cap 218 of the waste liquid recovery unit 217 is elevated to air-tightly cover the nozzles 233 of the nozzle units 213(1) to 213(3) (see FIG. 13). At this time, the waste liquid recovery pump 219 is driven so that the cleaning liquids are sucked from the nozzle units 213(1) to 213(3) through the nozzle 233, and the cleaning liquids are recovered. In this way, the storing portions 231 in the nozzle units 213(1) to 213(3), the pressure generating passage 234, and the nozzles 233 are cleaned.

Figure 15A:
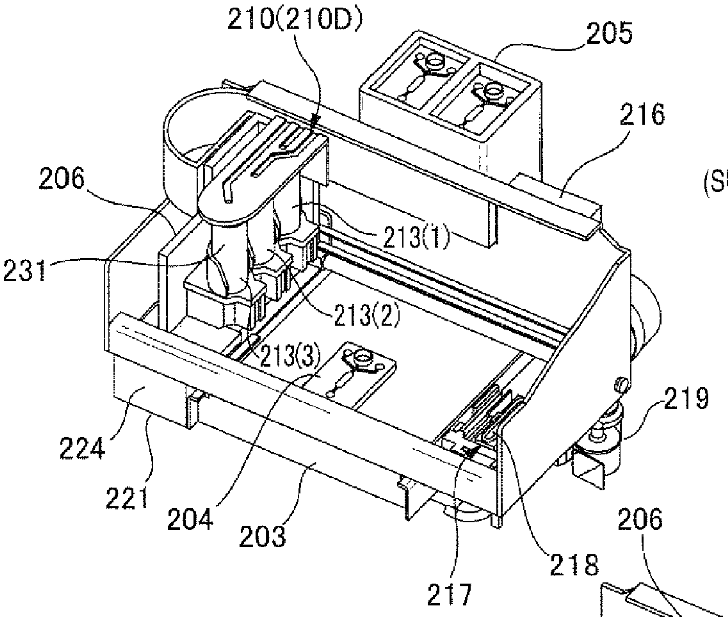
FIGS. 15A, 15B, and 15C are diagrams for explaining the dispensation operation of the clinical inspection device shown in FIG. 11.

Afterward, as shown in FIG. 15A, the liquid droplet ejecting head 210 is moved to the chemical liquid suction position 210D by the head carriage 206 so that the nozzles 233 of the nozzle units 213(1) to 213(3) can be positioned in positions among the wells in the second to fifth rows, which are chemical liquid storing portions. At this time, the well plate 223 is elevated by the elevation unit 224 so that the nozzles 233 are put in the chemical liquids stored by the wells. Subsequently, the head suction pump 216 is driven so that the storing portions of the nozzle units 213(1) to 213(3) become in a negative pressure state. In this way, the chemical liquids are sucked into the storing portions 231 of the nozzle units 213(1) to 213(3) through the nozzles 233. For example, the index chemical, the reaction chemical, and the buffer chemical are sucked into the storing portions 231 of the nozzle units 213(1) to 212(3), respectively.

Figure 15B:
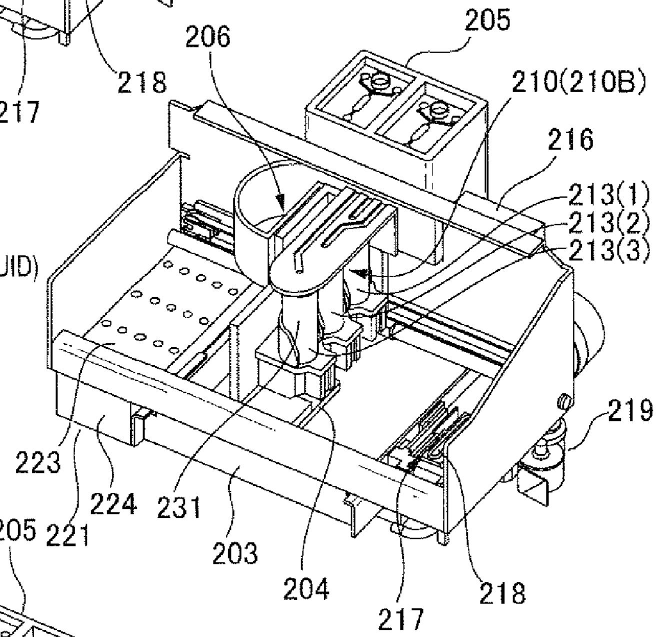

Subsequently, as shown in FIG. 15B, the liquid droplet ejecting head 210 is moved to the dispensation position 210B by the head carriage 206 to eject the chemical liquids from the nozzles 233 to the inspection chip 204 as many times as necessary. In this way, each of the chemical liquids is dispensed to the inspection chip 204. For example, the nozzles 233 of the nozzle units 213(1) to 213(3) of the liquid droplet ejecting head 210 are sequentially positioned in the ejection positions to eject the chemical liquids from the nozzles 233. The ejection positions between the nozzles 233 and the inspection chip 204 are determined by moving the inspection table 203 in the Y direction. Afterward, the liquid droplet ejecting head 210 is returned to the standby position.

By repeating the inspection introduction shown in FIG. 14A, the chemical liquids suction shown in FIG. 15A, and the chemical dispensation operation shown in FIG. 15B, each of the chemical liquids can be dispensed to the pieces of the inspection chip 204.

Figure 15C:
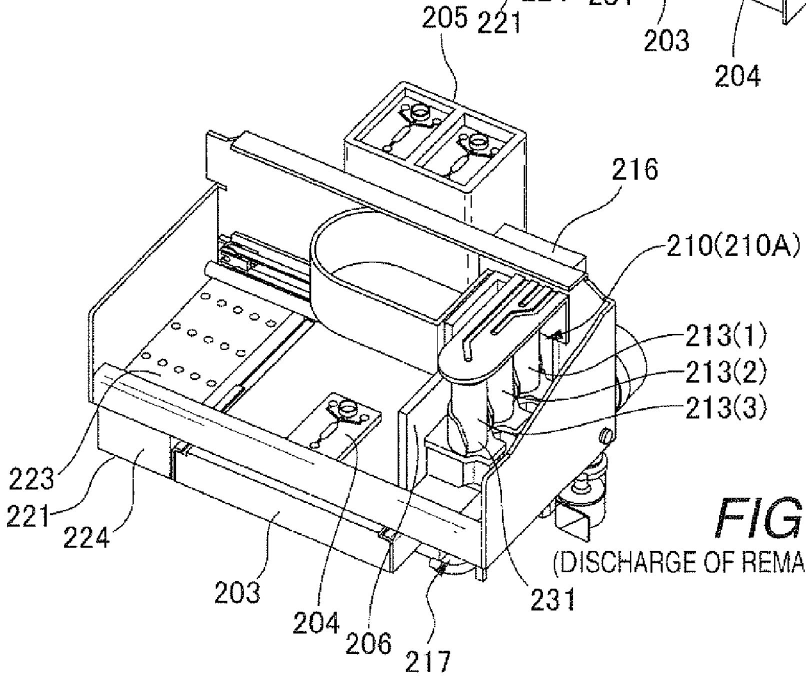

After the dispensation of the chemical liquids ends, as shown in FIG. 15C, the liquid droplet ejecting head 210 returns to the standby position. In addition, the cap 218 of the waste liquid recovery unit 217 is elevated to air-tightly cover the nozzles 233 of the nozzle units 213(1) to 213(3) (see FIG. 13). At this time, by driving the waste liquid recovery pump 219, the chemical liquids remaining in the nozzle units 213(1) to 213(3) are extracted through the nozzles 233 to be recovered. The empty nozzle units 213(1) to 213(3) of which uses are finished are detached from the driving units 211(1) to 211(3) and are discarded.

The chemical liquids such as the index chemical and the reaction chemical are dispensed by using the liquid droplet ejecting head 210 of an ink jet type. In addition, it is possible to also dispense the inspection object to the inspection chip 204 using the liquid droplet ejecting head 210. In the described exemplary embodiment, the liquid droplet ejecting head 210 includes the three nozzle units; however, one, two, four or more nozzle units can be also configured.

In this embodiment, the liquid droplet ejecting head is applied to a clinical inspection device, but may be applied to other inspection devices in the same manner. For example, the invention may be applied to an inspection device such as a gas chromatography, a high performance liquid chromatography (HPLC), and the like for precisely injecting a fixed amount of sample or test reagent.

As described above, the clinical inspection device according to the embodiment dispenses the chemical liquids by ejecting the liquid droplets from the nozzles using the liquid droplet ejecting head of the same mechanism as an ink jet head used in an ink jet printer. Accordingly, it is possible to control a small amount of chemical that is dispensed with high precision, thereby inspecting the inspection object with high precision.

Moreover, when the test reagent or the inspection object is exchanged to be inspected, the nozzle units are exchanged with new nozzle units by extracting the nozzle units from the driving units. Cleaning or the like of the dispenser is not required.

Since the actuator is mounted in the used nozzle units detached from the driving units, the nozzle units can be configured at low cost. Accordingly, even though the nozzle units are disposable, the assembly remains cost efficient. Moreover, since the actuator is not configured to come in contact, durability is also excellent.

In the method of using the clinical inspection device, the chemical liquids remaining in the used nozzle units are sucked into the waste liquid recovery unit to be recovered, and then the used nozzle units are discarded. As a result, there is an advantage in that environmental contamination does not occur.

In addition, when new empty nozzle units are mounted, the cleaning liquids are sucked and discharged repeatedly before suction of the chemical liquids to get rid of foreign substances or the like. As a result, it is possible to suppress any influence such as deterioration of inspection precision or the like caused by contamination of the inspection object or the test reagents due to foreign substances attached to the empty nozzle units.

This application claims priority from Japanese Patent Application Nos. 2006-302480 filed on Nov. 8, 2006, 2007-020555 filed on Jan. 31, 2007, and 2007-020556 filed on Jan. 31, 2007, the entire disclosures of which are expressly incorporated by reference herein.

While this invention has been described in conjunction with the specific embodiments thereof, it is evident that many alternatives, modifications, and variations will be apparent to those skilled in the art. Accordingly, preferred embodiments as set forth herein are intended to be illustrative, not limiting. There are changes that may be made without departing from the sprit and scope of the invention.

What is claimed is:

1. A liquid droplet ejecting head comprising:

a nozzle unit having a nozzle capable of ejecting liquid droplets and a pressure generating passage communicating with the nozzle; and a driving unit having a nozzle unit mounting portion and an actuator, wherein the nozzle unit is detachably mounted on the nozzle unit mounting portion, and wherein the actuator changes an inner volume of the pressure generating passage in order to eject the liquid droplets from the nozzle of the nozzle unit mounted on the nozzle unit mounting portion, wherein the nozzle unit has a mount portion detachably mounted on the nozzle unit mounting portion of the driving unit, wherein the mount portion has the pressure generating passage and a passage-side vibration plate that constitutes a part of the pressure generating passage and can vibrate in an out-of-plane direction, wherein the nozzle unit mounting portion comprises a mount hole, the driving unit further comprising a driving-side vibration plate that is disposed in the mount hole and can vibrate in the out-of-plane direction, wherein the actuator comprises a piezoelectric element, and wherein the driving-side vibration plate is disposed at a position that comes in contact with the passage-side vibration plate of the mount portion inserted into the mount hole so as to be vibrated by the piezoelectric element.

2. The liquid droplet ejecting head according to claim 1, wherein the driving unit has an elastic member disposed in a position opposite the driving-side vibration plate in the mount hole such that the elastic member is elastically deformed by the mount portion of the nozzle unit inserted into the mount hole and the mount portion can be urged toward the driving-side vibration plate by an elastically restoring force.

3. The liquid droplet ejecting head according to claim 2, wherein the passage-side vibration plate has a center portion of which a rigidity is higher than that of an outer peripheral portion and a flat contact surface formed in the center portion, wherein the contact surface can come in contact with the driving-side vibration plate, wherein the driving-side vibration plate has an opposite surface opposite the contact surface and a plurality of protrusions formed on the opposite surface, and wherein the protrusions can come in contact with the contact surface.

4. The liquid droplet ejecting head according to claim 3, wherein a back surface of the opposite surface of the driving-side vibration plate is retained so as to come in contact with a displacement surface of the piezoelectric element.

5. The liquid droplet ejecting head according to claim 4, wherein the piezoelectric element is a stacked piezo element.

6. The liquid droplet ejecting head according to claim 1, wherein the nozzle unit has a storing portion for storing liquid supplied to the pressure generating passage.

7. A multiple liquid droplet ejecting head comprising a plurality of liquid droplet ejecting heads as defined in claim 1, wherein the driving units of the liquid droplet ejecting heads are connected to each other.

8. An inspection device comprising a liquid droplet ejecting head for dispensing a test reagent or an inspection object, wherein the liquid droplet ejecting head comprises:

at least one nozzle unit having a nozzle capable of ejecting liquid droplets, a storing portion for storing the test reagent or the inspection object, and a pressure generating passage for supplying the test reagent or the inspection object from the storing portion to the nozzle; and at least one driving unit having a nozzle unit mounting portion and an actuator, wherein the nozzle unit is detachably mounted on the nozzle unit mounting portion, and wherein the actuator changes an inner volume of the pressure generating passage in order to eject the liquid droplets from the nozzle with the nozzle unit mounted on the nozzle unit mounting unit wherein the nozzle unit has a mount portion that is detachably mounted on the nozzle unit mounting portion of the driving unit, wherein the mount portion has the pressure generating passage and a passage-side vibration plate that constitutes a part of the pressure generating passage and can vibrate in an out-of-plane direction, wherein the nozzle unit mounting portion comprises a mount hole, the driving unit further comprising a driving-side vibration plate that is disposed in the mount hole and can vibrate in the out-of-plane direction, wherein the actuator comprises a piezoelectric element, and wherein the driving-side vibration plate is disposed in a position that comes in contact with the passage-side vibration plate of the mount portion inserted into the mount hole so as to be vibrated by the piezoelectric element.

9. The inspection device according to claim 8, further comprising a carriage conveying the driving unit to a mount position in which the nozzle unit is mounted on the driving unit and a dispensation position in which the test reagent or the inspection object is ejected from the nozzle with the nozzle unit mounted on the driving unit.

10. The inspection device according to claim 9, further comprising an inspection table for placing an inspection chip that receives the liquid droplets ejected from the liquid droplet ejecting head in the dispensation position.

11. The inspection device according to claim 10, further comprising a magazine for housing the nozzle unit and a nozzle unit conveyance mechanism for extracting the nozzle unit from the magazine to mount the nozzle unit in the driving unit.

12. The inspection device according to claim 11, further comprising a multiple driving unit including a plurality of driving units connected with each other, wherein the multiple driving unit is mounted on the carriage.

13. The inspection device according to claim 1, wherein the driving unit has an elastic member disposed in a position opposite the driving-side vibration plate in the mount hole such that the elastic member is elastically deformed by the mount portion of the nozzle unit inserted into the mount hole and the mount portion can be urged toward the driving-side vibration plate by an elastically restoring force.

14. The inspection device according to claim 13, wherein the passage-side vibration plate has a center portion of which a rigidity is higher than that of an outer peripheral portion and a flat contact surface formed in the center portion, wherein the contact surface can come in contact with the driving-side vibration plate, wherein the driving-side vibration plate has an opposite surface opposite the contact surface and a plurality of protrusions formed on the opposite surface, and wherein the protrusions can come in contact with the contact surface.

15. The inspection device according to claim 14, wherein a rear surface of the opposite surface of the driving-side vibration plate is retained so as to come in contact with a displacement surface of the piezoelectric element.

16. The inspection device according to claim 15, wherein the piezoelectric element is a stacked piezo element.

17. An inspection device comprising:

a liquid droplet ejecting head having a nozzle for ejecting and sucking liquid;

a carriage conveying the liquid droplet ejecting head to a standby position, a liquid ejection position, and a liquid suction position;

a liquid storing portion that stores liquid sucked by the liquid droplet ejecting head in the liquid suction position;

an inspection table that places an inspection chip that receives liquid droplets ejected from the liquid ejecting head in the liquid droplet ejection position; and a head sucking pump that supplies a sucking force required to suck the liquid by the nozzle to the liquid droplet ejecting head, wherein the liquid droplet ejecting head has:

at least one nozzle unit having the nozzle and a pressure generating passage communicating with the nozzle; and at least one driving unit having a nozzle unit mounting portion and an actuator, and wherein the nozzle unit is detachably mounted on the nozzle unit mounting portion, and wherein the actuator changes an inner volume of the pressure generating passage in order to eject the liquid droplets from the nozzle with the nozzle unit mounted on the nozzle unit mounting portion.

18. The inspection device according to claim 17, further comprising a waste liquid recovery portion that recovers liquid by sucking the liquid in the nozzle unit through the nozzle in the standby position.

19. The inspection device according to claim 18, wherein the liquid storing portion has a chemical liquid storing portion that stores a chemical liquid for inspecting an inspection object and a cleaning liquid storing portion that stores a cleaning liquid for cleaning the liquid droplet ejecting head.

20. The inspection device according to claim 19, wherein the carriage moves the liquid droplet ejecting head along a straight head movement route from the standby position to the liquid suction position via the liquid ejection position.

21. The inspection device according to claim 20, wherein the inspection device has an inspection chip supply mechanism moving the inspection table in a different direction from the head movement route.

22. The inspection device according to claim 21, wherein the liquid droplet ejecting head has a plurality of the driving units and the nozzle units, and wherein the liquid droplet ejecting head has the liquid storing portions corresponding to at least the number of the nozzle units.

23. The inspection device according to claim 17, wherein the nozzle unit has a mount portion detachably mounted on the nozzle unit mounting portion of the driving unit, wherein the mount portion has the pressure generating passage and a passage-side vibration plate that constitutes a part of the pressure generating passage and can vibrate in an out-of-plane direction, wherein the nozzle unit mounting portion comprises a mount hole, the driving unit further comprising a driving-side vibration plate that is disposed in the mount hole and can vibrate in the out-of-plane direction, wherein the actuator comprises a piezoelectric element, and wherein the driving-side vibration plate is disposed in a position that comes in contact with the passage-side vibration plate of the mount portion inserted into the mount hole so as to be vibrated by the piezoelectric element.

24. The inspection device according to claim 23, wherein the driving unit has an elastic member disposed in a position opposite the driving-side vibration plate in the mount hole such that the elastic member is elastically deformed by the mount portion of the nozzle unit inserted into the mount hole and the mount portion can be urged toward the driving-side vibration plate by an elastically restoring force.

25. The inspection device according to claim 24, wherein the passage-side vibration plate has a center portion of which a rigidity is higher than that of an outer peripheral portion and a contact surface formed in the center portion, wherein the contact surface can come in contact with the driving-side vibration plate, wherein the driving-side vibration plate has an opposite surface opposite the contact surface and a plurality of protrusions formed on the opposite surface, and wherein the protrusions can come in contact with the contact surface.

26. The inspection device according to claim 25, wherein a rear surface of the opposite surface of the driving-side vibration plate is retained to come in contact with a displacement surface of the piezoelectric element.

27. The inspection device according to claim 26, wherein the piezoelectric element is a stacked piezo element.

* * * * *